(12) United States Patent
Adams et al.

(10) Patent No.: US 9,873,735 B2
(45) Date of Patent: Jan. 23, 2018

(54) METHOD OF TREATMENT WITH ANTIBODIES HAVING SPECIFICITY FOR HUMAN OX40

(71) Applicant: UCB Biopharma SPRL, Brussels (BE)

(72) Inventors: Ralph Adams, Slough (GB); Pallavi Bhatta, Slough (GB); Sam Philip Heywood, Slough (GB); David Paul Humphreys, Slough (GB)

(73) Assignee: UCB Biopharma Sprl, Brussels (BE)

( * ) Notice: Subject to any disclaimer, the term of this patent is extended or adjusted under 35 U.S.C. 154(b) by 0 days.

(21) Appl. No.: 14/697,142

(22) Filed: Apr. 27, 2015

(65) Prior Publication Data

US 2016/0031974 A1 Feb. 4, 2016

Related U.S. Application Data

(62) Division of application No. 13/672,077, filed on Nov. 8, 2012, now Pat. No. 9,040,048.

(60) Provisional application No. 61/558,545, filed on Nov. 11, 2011.

(51) Int. Cl.
| | | |
|---|---|---|
| A61K 39/395 | (2006.01) | |
| C07K 16/18 | (2006.01) | |
| C07K 16/28 | (2006.01) | |
| A61K 39/00 | (2006.01) | |

(52) U.S. Cl.
CPC .......... *C07K 16/18* (2013.01); *A61K 39/3955* (2013.01); *C07K 16/2866* (2013.01); *C07K 16/2878* (2013.01); *A61K 2039/505* (2013.01); *C07K 2317/31* (2013.01); *C07K 2317/55* (2013.01); *C07K 2317/622* (2013.01); *C07K 2317/624* (2013.01); *C07K 2317/64* (2013.01); *C07K 2317/73* (2013.01); *C07K 2317/76* (2013.01); *C07K 2317/92* (2013.01); *C07K 2317/94* (2013.01)

(58) Field of Classification Search
CPC ................................................. A61K 39/3955
See application file for complete search history.

(56) References Cited

U.S. PATENT DOCUMENTS

| | | | |
|---|---|---|---|
| 4,741,900 | A | 5/1988 | Alvarez et al. |
| 5,219,996 | A | 6/1993 | Bodmer et al. |
| 5,585,089 | A | 12/1996 | Queen et al. |
| 5,677,425 | A | 10/1997 | Bodmer et al. |
| 6,277,962 | B1 | 8/2001 | Godfrey et al. |
| 2004/0146948 | A1 | 7/2004 | Britton et al. |
| 2005/0181448 | A1 | 8/2005 | Popplewell et al. |
| 2006/0228358 | A1 | 11/2006 | Lawson et al. |
| 2007/0110747 | A1 | 5/2007 | Paszty et al. |
| 2007/0224627 | A1 | 9/2007 | Horowitz et al. |
| 2008/0069822 | A1 | 3/2008 | Jensen et al. |

FOREIGN PATENT DOCUMENTS

| | | |
|---|---|---|
| CN | 102164965 | 8/2011 |
| EP | 0392745 | 10/1990 |
| WO | 86/01533 | 3/1986 |
| WO | 89/00195 | 1/1989 |
| WO | 89/01476 | 2/1989 |
| WO | 91/09967 | 7/1991 |
| WO | 92/22583 | 12/1992 |
| WO | 93/06231 | 4/1993 |
| WO | 98/20734 | 5/1998 |
| WO | 98/025971 | 6/1998 |
| WO | 03/031581 | 4/2003 |
| WO | 2005/061540 | 7/2005 |
| WO | 2006/029879 | 3/2006 |
| WO | 2006/131951 | 12/2006 |
| WO | 2007/062245 | 5/2007 |
| WO | 2008/106116 | 9/2008 |
| WO | 2009/040562 | 4/2009 |
| WO | 2010/035012 | 4/2010 |
| WO | 2010/096418 | 8/2010 |
| WO | 2011/030107 | 3/2011 |
| WO | 2011/036460 | 3/2011 |
| WO | 2011/086091 | 7/2011 |
| WO | 2011/096418 | 8/2011 |
| WO | 2013/068571 | 5/2013 |

OTHER PUBLICATIONS

Altschul, S.F. et al., "Basic Local Alignment Search Tool," J. Mal. Biol., vol. 215, pp. 403-410, 1990.
Altschul, S.F. et al., "Gapped BLAST and PSI-BLAST: A New Generation of Protein Database Search Programs," Nucleic Acids Res., vol. 25, pp. 3389-3402, 1997.
Arestides, R. et al., "Costimulatory molecule OX40L is critical for both Th1 and Th2 responses in allergic inflammation," Eur. J. Immunol., vol. 32, pp. 2874-2880, 2002.
Bach, F. et al., "Lymphocyle Interaction: A Potential Histocompatibility Test in vitro," vol. 143, pp. 813-814 (1964).
Bansal-Pakala, P. et al., "Costimulation of CDS T Cell Response by OX40," J. Immunol., vol. 172, pp. 4821-4825, 2004.
Boomer, J.L. et al., "The molecular architecture of the TNF superfamily," Trends Biochem. Sci., vol. 27, No. 1, pp. 19-26, 2002.
Bromelow, K.V. et al., "Whole blood assay for assessment of the mixed lymphocyle reaction," J. Immunol. Meth., vol. 247, pp. 1-8, 2001.
Brugnoni, D. et al., "CD134/0X40 Expression by Synovial Fluid CD4+ T Lymphocyles in Chronic Synovitis," Br. J. Rheum., vol. 37, No. 5, pp. 584-585, 1998.
Burgess, J. et al., "CD40 and OX40 ligand are increased on stimulated asthmatic airway smooth muscle," J. Allergy Clin. Immunol., vol. 115, No. 2, pp. 302-308, 2005.
Burgess, J. et al., "Detection and characterization of OX40 ligand expression in human airway smooth muscle cells: A possible role in asthma?" J. Allergy Clin. Immunol., vol. 113, No. 4, pp. 683-689, 2004.

(Continued)

*Primary Examiner* — Prema Mertz
(74) *Attorney, Agent, or Firm* — Fish & Richardson P.C.

(57) ABSTRACT

The invention relates to antibody molecules having specificity for antigenic determinants of human OX40, therapeutic uses of the antibody molecules and methods for producing said antibody molecules.

50 Claims, 17 Drawing Sheets

(56) References Cited

OTHER PUBLICATIONS

Carboni, S. et al., "CD134 plays a crucial role in the pathogenesis of EAE and is upregulated in the CNS of patients with multiple sclerosis," J. Neuroimmunology, vol. 145, pp. 1-11, 2003.
Chothia, C. et al., "Canonical Structures for the Hypervariable Regions of Immunoglobulins," J. Mal. Biol., vol. 196, pp. 901-917, 1987.
Compaan, D. et al., "The Crystal Structure of the Costimulatory OX40-OX4OL Complex," Structure, vol. 14, pp. 1321-1330, 2006.
Crameri, A. et al., "DNA Shuffling of a Family of Genes from Diverse Species Accelerated Directed Evolution," Nature, vol. 391, pp. 288-291, 1998.
Dubowchik, G.M. et al., "Receptor-Mediated and Enzyme-Dependent Targeting of Cytotoxic Anticancer Drugs," Pharmacology and Therapeutics, vol. 83, pp. 67-123, 1999.
Giacomelli, R. et al., "T lymphocyles in the synovial fluid of patients with active rheumatoid arthritis display CD134-0X40 surface antigen," Clin. Exp. Rheumatol., vol. 19, pp. 317-320, 2001.
Gish, W. et al., "Identification of Protein Coding Regions by Database Similarity Search," Nature Genet., vol. 3, pp. 266-272, 1993.
Gramaglia, I. et al., "Ox-40 Ligand. A Potential Costimulatory Molecule for Sustaining Primary CD4 T Cell Responses," J. Immunol., vol. 161, pp. 6510-6517, 1998.
Gramaglia, I. et al., "The OX40 Costimulatory Receptor Determines the Development of CD4 Memory by Regulating Primary Clonal Expansion," J. Immunol., vol. 165, pp. 3043-3050, 2000.
Hoshino, A. et al., "Critical role for OX40 ligand in the development of pathogenic Th2 cells in a murine model of asthma," Eur. J. Immunol., vol. 33, pp. 861-869, 2003.
Imura, A. et al., "The Human OX40/gp34 System Directly Mediates Adhesion of Activated T Cells to Vascular Endothelial Cells," J. Exp. Med., vol. 183, pp. 2185-2195, 1996.
Irving et al. Affinity maturation of recombinant antibodies using E. coli mutator cells. Immunotechnology. 1996; 2:127-143.
Jember, A. et al., "Development of Allergic Inflammation in a Murine Model of Asthma Is Dependent on the Costimulatory Receptor OX40," J. Exp. Med, vol. 193, No. 3, pp. 387-392, 2001.
Jordan, W. et al., "Optimal analysis of composite cylokine responses during alloreactivity," J. Immunol. Meth., vol. 260, pp. 1-14, 2002.
Kashmiri V.S. et al., "SDR grafting—a new approach to antibody humanization," Methods, vol. 36, pp. 25-34, 2005.
Low, N.M. et al., "Mimicking Somatic Hypermutation Affinity Maturation of antibodies Displayed on Bacteriophage Using a Bacterial Mutator Strain," J. Mal. Biol., vol. 250, pp. 359-368, 1996.
Lukacs, N. et al., "The Production of Chemotactic Cylokines in an Allogenic Response," AJP, vol. 143, No. 4, 1993.
Madden, T.L. et al., "Applications of Network BLAST Server," Meth. Enzymol., vol. 266, pp. 131-141, 1996.
Malmstrom, V. et al., "CD134L Expression on Dendritic Cells in the Mesenteric Lymph Nodes Drives Colitis in T Cell-Restored SCIO Mice," J. Immunol., vol. 166, pp. 6972-6981, 2001.
Marks, J.D. et al., "By-passing Immunization. Building High Affinity Human Antibodies by Chain Shuffling," Bio/Technology, vol. 10, pp. 779-783, 1992.
Nohara, C. et al., "Amelioration of Experimental Autoimmune Encephalomyelitis with Anti-OX40 Ligand Monoclonal Antibody: A Critical Role for OX40 Ligand in Migration, But Not Development, of Pathogenic T Cells," J. Immunol., vol. 166, pp. 2108-2115, 2001.
O'Flaherty, E. et al., "Regulation of T-cell apoptosis: a mixed lymphocy le reaction model," Immunology, vol. 100, pp. 289-299, 2000.
Pakala, S. et al., "Prevention of diabetes in NOD mice at a late stage by targeting OX40/0X40 ligand interactions," Eur. J. Immunol., vol. 34, pp. 3039-3046, 2004.
Patschan et al., "CD134 expression on CD4+ T cells is associated with nephritis and disease activity in patients with systemic lupus ery1hematosus," Clin. Exp. Immunol., vol. 145, pp. 235-242, 2006.

Patten, P.A. et al., "Applications of DNA Shuffling to Pharmaceuticals and Vaccines," Curr. Opin. Biotechnol., vol. 8, pp. 724-733, 1997.
Riechmann, L. et al., "Reshaping human antibodies for therapy," Nature, vol. 332, pp. 323-327, 1988.
Salek-Ardakani, S. et al., "OX40 (CD134) Controls Memory of T Helper 2 Cells that Drive Lung Inflammation," J. Exp. Med., vol. 198, No. 2pp. 315-324, 2003.
Seshasayee, D. et al., "In vivo blockade of OX40 ligand inhibits thymic stromal lymphopoetin driven atopic inflammation," J. Clin. Invest., vol. 117, No. 12,pp. 3868-3878, 2007.
Sherman, L. et al., The Molecular Basis of Allorecognition, Annu. Rev. Immunol., vol. 11, pp. 385-402, 1993.
Souza, H. et al., "Expression of lymphocyle-endothelial receptor-ligand pairs, a4J37/MAdCAM-1 and OX40/0X40 ligand in the colon and jejunum of patients with inflammatory bowel disease," Gut, vol. 45, pp. 856-863, 1999.
Stuber, E. et al., "The expression of OX40 in immunologically mediated diseases of the gastrointestinal tract (celiac disease, Crohn's disease, ulcerative colitis)," Eur. J. Clin. Invest., vol. 30, pp. 594-599, 2000.
Stuber, E. et al., "The T Cell-B Interaction via OX40-0X40L Is Necessary for the T Cell-dependent Humoral Immune Response," J. Exp. Med., vol. 183, pp. 979-989, 1996.
Taylor, L. et al., "Identification of a soluble OX40 isoform: development of a specific and quantitative immunoassay," J. Immunol. Methods, vol. 255, pp. 67-72, 2001.
Thompson, J. et al., "Affinity Maturation of a High-affinity Human Monoclonal Antibody Against the Third Hypervariable Loop of Human Immunodeficiency Virus: Use of Phage Display to Improve Affinity and Broaden Strain Reactivity," J. Mal. Biol. vol. 256 pp. 77-88 1996.
Thorpe, P.E. et al., "The Preparation and Cylotoxic Properties of Antibody-Toxin Conjugates," Immunol. Rev., vol. 62, pp. 119-158, 1982.
Totsuka, T. et al., "Therapeutic effect of anti-OX4OL and anti-TNF-a MAbs in a murine model of chronic colitis," Am. J. Physiol. Gastrointest. Liver Physiol., vol. 284, pp. G595-G603, 2003.
Vaughan, T.J. et al., "Human Antibodies by Design," Nature Biotechnology, vol. 16, No. 6, pp. 535-539, 1998.
Whittle, N. et al., "Expression in COS cells of a mouse-human chimaeric B72.3 antibody," Protein Eng., vol. 1, No. 6, pp. 499-505, 1987.
Yang, W-P. et al., "CDR Walking Mutagenesis for the Affinity Maturation of a Potent Human Anti-HIV-1 Antibody into the Picomolar Range," J. Mal. Biol., vol. 254, pp. 392-403, 1995.
Yoshioka, T. et al., "Contribution of OX40/0X40 ligand interaction to the pathogenesis of rheumatoid arthritis," Eur. J. Immunol., vol. 30, pp. 2815-2823, 2000.
Zhang, J. et al., "PowerBLAST: A New Network BLAST Application for Interactive or Automated Sequence Analysis and Annotation," Genome Res., vol. 7, pp. 649-656, 1997.
Holt et al., "Anti-serum albumin domain antibodies for extending the half-lives of short lived drugs," Protein Engineering, Design & Selection, Apr. 2, 2008, vol. 21 No. 6 pp. 283-288.
Singapore Search Report and Written Opinion for Application No. 11201402093R, dated Nov. 19, 2015, 7 pages.
Chile Office Action for Application No. 2014-01193, dated Apr. 12, 2016, 7 pages.
Japanese Office Action for Application No. 2014-540489, dated Aug. 30, 2016, 6 pages (With English Translation).
Gulf Coop Council Office Action for Application No. GC 2012-22753, dated Apr. 21, 2016, 7 pages (With English Translation).
Chinese Office Action for Application No. 201280055398.8, dated Sep. 7, 2015, 12 pages (With English Translation).
English Translation of Taiwan Office Action for Application No. 101141760, dated Aug. 25, 2016, 7 pages.
Chilean National Institute for Intellectual Property, Chile Office Action for Counterpart Application No. 2014-0119, dated Jan. 5, 2017.
European Patent Office, European Search Report for Application No. 12803508.6, dated Feb. 17, 2017, 8 pp.

(56) References Cited

OTHER PUBLICATIONS

Intellectual Property Office of Singapore, Singapore Search Report and Written Opinion for Application No. 11201402093R, dated Feb. 14, 2017, 17 pp.
Kontermann., "Strategies to extend plasma half-lives of recombinant antibodies," BioDrugs. 2009, 23(2): 93-109, 2009.
Wikipedia—Adalimumab, Retrieved from https://en.wikipedia.org/w/index.php?title=Adalimumab&oldid=769429082, last modified Mar. 9, 2017, retrieved Mar. 30, 2017, 5 pp.
Wikipedia—Corticosteroid. Retrieved from https://en.wikipedia.org/w/index.php?title=Corticosteroid&oldid=768588837, last modified Mar. 4, 2017, retrieved Mar. 30, 2017, 7 pp.
Wikipedia—Tacrolimus, Retrieved from https://en.wikipedia.org/w/index.php?title=Tacrolimus&oldid=771882948, last modified Mar. 24, 2017, retrieved Mar. 30, 2017, 10 pp.

First Variable region of light chain VL1
First Variable region of heavy chain VH1
Constant regions cKappa ■ and CH1 ☐
Second variable region of light chain VL2
Second variable region of heavy chain VH2

Disulphide bond

Fig. 2A
Light chain variable region of antibody A26 (SEQ ID NO:7)
DIQMTQSPSSLSASVGDRVTITCRATQSIYNALAWYQQKPGKAPKLLIYNANTLHTGVPSRFSA
SGSGTDSTLTISSLQPEDFATYYCQQYYDYPLTFGGGTKVEIKR Fig. 2B
Heavy chain variable region of antibody A26 (SEQ ID NO:8)
EVQLVESGGGLVQPGGSLRLSCAASGFTFTNYGIHWIRQAPGKGLEWVASISPSGGLTYYRDSV
KGRFTISRDDAKNSPYLQMNSLRAEDTAVYYCATGGEGIFDYWGQGTLVTVSS

Fig. 2C

| | |
|---|---|
| CDRH1: | NYGIH (SEQ ID NO:1) |
| CDRH2: | SISPSGGLTYYRDSVKG (SEQ ID NO:2) |
| CDRH3: | GGEGIFDY (SEQ ID NO:3) |
| CDRL1: | RATQSIYNALA (SEQ ID NO:4) |
| CDRL2: | NANTLHT (SEQ ID NO:5) |
| CDRL3: | QQYYDYPLT (SEQ ID NO:6) |

Fig. 2D
Light chain of anti-OX40 antibody Fab component (SEQ ID NO:9)
DIQMTQSPSSLSASVGDRVTITCRATQSIYNALAWYQQKPGKAPKLLIYNANTLHTGVPSRFSA
SGSGTDSTLTISSLQPEDFATYYCQQYYDYPLTFGGGTKVEIKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGEC Fig. 2E
Heavy chain of anti-OX40 antibody Fab component (SEQ ID NO:10)
EVQLVESGGGLVQPGGSLRLSCAASGFTFTNYGIHWIRQAPGKGLEWVASISPSGGLTYYRDSV
KGRFTISRDDAKNSPYLQMNSLRAEDTAVYYCATGGEGIFDYWGQGTLVTVSSASTKGPSVFPL
APSSKSTSGGTAALGCLVKDYFPEPVTVSWNSGALTSGVHTFPAVLQSSGLYSLSSVVTVPSSS
LGTQTYICNVNHKPSNTKVDKKVEPKSC

Fig. 3A

Heavy chain of anti-albumin Fv component (SEQ ID NO:11)

EVQLLESGGGLVQPGGSLRLSCAVSGIDLSNYAINWVRQAPGKCLEWIGIIWASGTTFYATWAKGRFTISRDNSKNT
VYLQMNSLRAEDTAVYYCARTVPGYSTAPYFDLWGQGTLVTVSS

Fig. 3B

Light chain of anti-albumin Fv component (SEQ ID NO:12)

DIQMTQSPSSVSASVGDRVTITCQSSPSVWSNFLSWYQQKPGKAPKLLIYEASKLTSGVPSRFSGSGSGTDFTLTIS
SLQPEDFATYYCGGGYSSISDTTFGCGTKVEIKRT

Fig. 3C

Linker 1 (SEQ ID NO:13)

SGGGGSGGGGTGGGGS

Fig. 3D

Linker 2 (SEQ ID NO:14)

GGGGSGGGGSGGGGS

Fig. 3E

A26 Fab Heavy-(G4S,G4T,G4S)-645dsFv(gH5) (SEQ ID NO:15)

EVQLVESGGGLVQPGGSLRLSCAASGFTFTNYGIHWIRQAPGKGLEWVASISPSGGLTYYRDSVKGRFTISRDDAKN
SPYLQMNSLRAEDTAVYYCATGGEGIFDYWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDKKVEPKSCSGGGGSGGGGT
GGGGSEVQLLESGGGLVQPGGSLRLSCAVSGIDLSNYAINWVRQAPGKCLEWIGIIWASGTTFYATWAKGRFTISRD
NSKNTVYLQMNSLRAEDTAVYYCARTVPGYSTAPYFDLWGQGTLVTVSS

Fig. 3F

A26 Fab Light-(3xG4S)-645dsFv(gL4) (SEQ ID NO:16)

DIQMTQSPSSLSASVGDRVTITCRATQSIYNALAWYQQKPGKAPKLLIYNAMTLHTGVPSRFSASGSGTDSTLTISS
LQPEDFATYYCQQYYDYPLTFGGGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGECGGGGSGGGGSGGGGSDI
QMTQSPSSVSASVGDRVTITCQSSPSVWSNFLSWYQQKPGKAPKLLIYEASKLTSGVPSRFSGSGSGTDFTLTISSL
QPEDFATYYCGGGYSSISDTTFGCGTKVEIKRT

Fig. 4A

645gH1 heavy chain variable domain (SEQ ID NO:17)

EVQLLESGGGLVQPGGSLRLSCAVSGIDLSNYAINWVRQAPGKCLEWIGIIWASGTTFYATWAKGRFTISRDSTTVY
LQMNSLRAEDTAVYYCARTVPGYSTAPYFDLWGQGTLVTVSS

Fig. 4B

645gL1 light chain variable domain (SEQ ID NO:18)

DIVMTQSPSSVSASVGDRVTITCQSSPSVWSNFLSWYQQKPGKAPKLLIYEASKLTSGVPSRFKGSGSGTDFTLTIS
SLQPEDFATYYCGGGYSSISDTTFGCGTKVEIK

Fig. 4C

A26 Fab Heavy-(3xG4S)-645dsFv(gH1) (SEQ ID NO:19)

EVQLVESGGGLVQPGGSLRLSCAASGFTFTNYGIHWIRQAPGKGLEWVASISPSGGLTYYRDSVKGRFTISRDDAKN
SFYLQMNSLRAEDTAVYYCATGGEGIFDYWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDKKVEPKSCSGGGGSGGGGS
GGGGSEVQLLESGGGLVQPGGSLRLSCAVSGIDLSNYAINWVRQAPGKCLEWIGIIWASGTTFYATWAKGRFTISRD
STTVYLQMNSLRAEDTAVYYCARTVPGYSTAPYFDLWGQGTLVTVSS

Fig. 4D

A26 Fab Light-(3xG4S)-645dsFv(gL1) (SEQ ID NO:20)

DIQMTQSPSSLSASVGDRVTITCRATQSIYNALAWYQQKPGKAPKLLIYNANTLHTGVPSRFSASGSGTDSTLTISS
LQPEDFATYYCQQYYDYPLTFGGGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGECSGGGGSGGGGSGGGGSD
IVMTQSPSSVSASVGDRVTITCQSSPSVWSNFLSWYQQKPGKAPKLLIYEASKLTSGVPSRFKGSGSGTDFTLTISS
LQPEDFATYYCGGGYSSISDTTFGCGTKVEIK

Fig. 5A

DNA encoding Heavy chain A26-645(gH5) including E.coli OmpA leader (SEQ ID NO:21)

ATGAAGAAGACTGCTATAGCGATCGCAGTGGCGCTAGCTGGTTTCGCCACCGTGGCGCAAGCTGAAGTTCAGCTGGT
CGAGTCTGGAGGCGGGCTTGTCCAGCCTGGAGGAGCCTGCGTCTCTCTTGTGCAGCAAGCGGTTTCACGTTCACCA
ACTACGGTATCCACTGGATTCGTCAGGCACCAGGTAAAGGTCTGGAATGGGTAGCCTCTATCTCTCCGTCTGGTGGT
CTGACGTACTACCGTGACTCTGTCAAAGGTCGTTTCACCATCTCTCGTGATGACGCGAAAAACTCTCCGTACCTGCA
AATGAACTCTCTGCGTGCAGAAGATACCGCAGTGTACTACTGCGCTACTGGTGGTGAAGGTATCTTCGACTACTGGG
GTCAGGGTACCCTGGTAACTGTCTCGAGCGCTTCTACAAAGGGCCCAAGCGTTTTCCCACTGGCTCCGTCCTCTAAA
TCCACCTCTGGTGGTACGGCTGCACTGGGTTGCCTGGTGAAAGACTACTTCCCAGAACCAGTTACCGTGTCTTGGAA
CTCTGGTGCACTGACCTCTGGTGTTCACACCTTTCCAGCAGTTCTCCAGTCTTCTGGTCTGTACTCCCTGTCTAGCG
TGGTTACCGTTCCGTCTTCTTCTCTGGGTACTCAGACCTACATCTGCAACGTCAACCACAAACCGTCCAACACCAAG
GTCGACAAAAAGTCGAGCCGAAATCCTGTAGTGGAGGTGGGGCTCAGGTGGAGGCGGGACCGGTGGAGGTGGCAG
CGAGGTTCAACTGCTTGAGTCTGGAGGAGGCCTAGTCCAGCCTGGAGGGAGCCTGCGTCTCTCTTGTGCAGTAAGCG
GCATCGACCTGAGCAATTACGCCATCAACTGGGTGAGACAAGCTCCGGGGAAGTGTTTAGAATGGATCGGTATAATA
TGGGCCAGTGGGACGACCTTTTATGCTACATGGGCGAAAGGAAGGTTTACAATTAGCCGGGACAATAGCAAAAACAC
CGTGTATCTCCAAATGAACTCCTTGCGAGCAGAGGACACGGCGGTGTACTATTGTGCTCGCACTGTCCCAGGTTATA
GCACTGCACCCTACTTCGATCTGTGGGACAAGGGACCCTGGTGACTGTTTCAAGTTAA

Fig. 5B

DNA encoding Heavy chain A26-645(gH5) (SEQ ID NO:22)

GAAGTTCAGCTGGTCGAGTCTGGAGGCGGGCTTGTCCAGCCTGGAGGGAGCCTGCGTCTCTCTTGTGCAGCAAGCGG
TTTCACGTTCACCAACTACGGTATCCACTGGATTCGTCAGGCACCAGGTAAAGGTCTGGAATGGGTAGCCTCTATCT
CTCCGTCTGGTGGTCTGACGTACTACCGTGACTCTGTCAAAGGTCGTTTCACCATCTCTCGTGATGACGCGAAAAAC
TCTCCGTACCTGCAAATGAACTCTCTGCGTGCAGAAGATACCGCAGTGTACTACTGCGCTACTGGTGGTGAAGGTAT
CTTCGACTACTGGGGTCAGGGTACCCTGGTAACTGTCTCGAGCGCTTCTACAAAGGGCCCAAGCGTTTTCCCACTGG
CTCCGTCCTCTAAATCCACCTCTGGTGGTACGGCTGCACTGGGTTGCCTGGTGAAAGACTACTTCCCAGAACCAGTT
ACCGTGTCTTGGAACTCTGGTGCACTGACCTCTGGTGTTCACACCTTTCCAGCAGTTCTCCAGTCTTCTGGTCTGTA
CTCCCTGTCTAGCGTGGTTACCGTTCCGTCTTCTTCTCTGGGTACTCAGACCTACATCTGCAACGTCAACCACAAAC
CGTCCAACACCAAGGTCGACAAAAAAGTCGAGCCGAAATCCTGTAGTGGAGGTGGGGCTCAGGTGGACGCGGGACC
GGTGGAGGTGGCAGCGAGGTTCAACTGCTTGAGTCTGGAGGAGGCCTAGTCCAGCCTGGAGGGAGCCTGCGTCTCTC
TTGTGCAGTAAGCGGCATCGACCTGAGCAATTACGCCATCAACTGGGTGAGACAAGCTCCGGGGAAGTGTTTAGAAT
GGATCGGTATAATATGGGCCAGTGGGACGACCTTTTATGCTACATGGGCGAAAGGAAGGTTTACAATTAGCCGGGAC
AATAGCAAAAACACCGTGTATCTCCAAATGAACTCCTTGCGAGCAGAGGACACGGCGGTGTACTATTGTGCTCGCAC
TGTCCCAGGTTATAGCACTGCACCCTACTTCGATCTGTGGGACAAGGGACCCTGGTGACTGTTTCAAGTTAA

Fig. 6A

DNA encoding Light chain A26-645(gL4) including E.coli OmpA leader (SEQ ID NO:23)

ATGAAAAAGACAGCTATCGCAATTGCAGTGGCGTTGGCTGGTTTCGCGACCGTTGCGCAAGCTGATATCCAGATGAC
CCAGAGCCCAAGCAGTCTCTCCGCCAGCGTAGGCGATCGTGTGACTATTACCTGTCGTGCAACCCAGAGCATCTACA
ACGCTCTGGCTTGGTATCAGCAGAAACGGGTAAAGCGCCAAAACTCCTGATCTACAACGCGAACACTCTGCATACT
GGTGTTCCGTCTCGTTTCTCTGCGTCTGGTTCTGGTACGGACTCTACTCTGACCATCTCCTCTCTCCAGCCGGAAGA
TTTCGCGACCTACTACTGCCAGCAGTACTACGATTACCCACTGACGTTTGGTGGTGGTACCAAAGTTGAGATCAAAC
GTACGGTTGCAGCTCCATCCGTCTTCATCTTTCCACCGTCTGACGAACAGCTCAAATCTGGTACTGCTTCTGTCGTT
TGCCTCCTGAACAACTTCTATCCGCGTGAAGCGAAAGTCCAGTGGAAAGTCGACAACGCACTCCAGTCTGGTAACTC
TCAGGAATCTGTGACCGAACAGGACTCCAAAGACTCCACCTACTCTCTGTCTAGCACCCTGACTCTGTCCAAAGCAG
ACTACGAGAAACACAAAGTGTACGCTTGCGAAGTTACCCATCAGGGTCTGAGCTCTCCGGTTACCAAATCCTTTAAT
AGAGGGGAGTGTGGTGGCGGTGGCAGTGGTGGTGGAGGTTCCGGAGGTGGCGGTTCAGACATACAAATGACCCAGAG
TCCTTCATCGGTATCCGCGTCCGTTGGCGATAGGGTGACTATTACATGTCAAAGCTCTCCTAGCGTCTGGAGCAATT
TTCTATCCTGGTATCAACAGAAACCGGGGAAGGCTCCAAAACTTCTGATTTATGAAGCCTCGAAACTCACCAGTGGA
GTTCCGTCAAGATTCAGTGGCTCTGGATCAGGGACAGACTTCACGTTGACAATCAGTTCGCTGCAACCAGAGGACTT
TGCGACCTACTATTGTGGTGGAGGTTACAGTAGCATAAGTGATACGACATTTGGGTGCGGTACTAAGGTGGAAATCA
AACGTACCTAA

Fig. 6B

DNA encoding Light chain A26-645(gL4) (SEQ ID NO:24)

GATATCCAGATGACCCAGAGCCCAAGCAGTCTCTCCGCCAGCGTAGGCGATCGTGTGACTATTACCTGTCGTGCAAC
CCAGAGCATCTACAACGCTCTGGCTTGGTATCAGCAGAAACGGGTAAAGCGCCAAAACTCCTGATCTACAACGCGA
ACACTCTGCATACTGGTGTTCCGTCTCGTTTCTCTGCGTCTGGTTCTGGTACGGACTCTACTCTGACCATCTCCTCT
CTCCAGCCGGAAGATTTCGCGACCTACTACTGCCAGCAGTACTACGATTACCCACTGACGTTTGGTGGTGGTACCAA
AGTTGAGATCAAACGTACGGTTGCAGCTCCATCCGTCTTCATCTTTCCACCGTCTGACGAACAGCTCAAATCTGGTA
CTGCTTCTGTCGTTTGCCTCCTGAACAACTTCTATCCGCGTGAAGCGAAAGTCCAGTGGAAAGTCGACAACGCACTC
CAGTCTGGTAACTCTCAGGAATCTGTGACCGAACAGGACTCCAAAGACTCCACCTACTCTCTGTCTAGCACCCTGAC
TCTGTCCAAAGCAGACTACGAGAAACACAAAGTGTACGCTTGCGAAGTTACCCATCAGGGTCTGAGCTCTCCGGTTA
CCAAATCCTTTAATAGAGGGGAGTGTGGTGGCGGTGGCAGTGGTGGTGGAGGTTCCGGAGGTGGCGGTTCAGACATA
CAAATGACCCAGAGTCCTTCATCGGTATCCGCGTCCGTTGGCGATAGGGTGACTATTACATGTCAAAGCTCTCCTAG
CGTCTGGAGCAATTTTCTATCCTGGTATCAACAGAAACCGGGGAAGGCTCCAAAACTTCTGATTTATGAAGCCTCGA
AACTCACCAGTGGAGTTCCGTCAAGATTCAGTGGCTCTGGATCAGGGACAGACTTCACGTTGACAATCAGTTCGCTG
CAACCAGAGGACTTTGCGACCTACTATTGTGGTGGAGGTTACAGTAGCATAAGTGATACGACATTTGGGTGCGGTAC
TAAGGTGGAAATCAAACGTACCTAA

Fig. 7A

DNA encoding Heavy chain A26-645(gH5) including B72.3 leader sequence (SEQ ID NO:25)

ATGGAATGGTCCTGGGTCTTCCTGTTTTTCCTTTCTGTCACAACCGGGGTGCACAGCGAGGTGCAGCTCGTCGAGTC
TGGAGGCGGGCTTGTCCAGCCTGGAGGGAGCCTGCGTCTCTCTTGTGCAGCAAGCGGTTTCACGTTCACCAACTACG
GTATCCACTGGATTCGTCAGGCACCAGGTAAACGTCTGGAATGGGTAGCCTCTATCTCTCCGTCTGGTGGTCTGACG
TACTACCGTGACTCTGTCAAAGGTCGTTTCACCATCTCTCGTGATGACGCGAAAAACTCTCCGTACCTGCAGATGAA
CTCTCTGCGTGCAGAAGATACCGCAGTGTACTACTGCGCTACTGGTGGTGAAGGTATCTTCGACTACTGGGGTCAGG
GTACCCTGGTAACTGTCTCAAGCGCTTCTACAAAGGGCCCATCGGTCTTCCCCCTGGCACCCTCCTCCAAGAGCACC
TCTGGGGGCACAGCGGCCCTGGGCTGCCTGGTCAAGGACTACTTCCCCGAACCGGTGACGGTGTCGTGGAACTCAGG
CGCCCTGACCAGCGGCGTGCACACCTTCCCGGCTGTCCTACAGTCCTCTGGACTCTACTCCCTCAGCAGCGTGGTGA
CCGTGCCCTCCAGCAGCTTGGGCACCCAGACCTACATCTGCAACGTGAATCACAAGCCCAGCAACACCAAGGTGGAC
AAGAAAGTTGAGCCCAAATCTTGTTCCGGAGGTGGCGGTTCCGGAGGTGGCGGTACCGGTGGCGGTGGATCCGAAGT
CCAGCTGCTTGAATCCGGAGGCGGACTCGTGCAGCCCGGAGGCAGTCTTCGCTTGTCCTGCGCTGTATCTGGAATCG
ACCTGAGCAATTACGCCATCAACTGGGTGAGACAGGCACCTGGGAAATGCCTCGAATGGATCGGCATTATATGGGCT
AGTGGCACCACCTTTTATGCTACATGGGCGAAGGGTAGATTCACAATCTCACGGGATAATAGTAAGAACACAGTGTA
CCTGCAGATGAACTCCCTGCGAGCAGAGGATACCGCCGTTTACTATTGTGCTCGCACTGTCCCAGGTTATAGCACTG
CACCCTACTTTGATCTGTGGGGCAGGGCACTCTGGTCACCGTCTCGAGTTGA

Fig. 7B

DNA encoding Heavy chain A26-645(gH5) (SEQ ID NO:26)

GAGGTGCAGCTCGTCGAGTCTGGAGGCGGGCTTGTCCAGCCTGGAGGGAGCCTGCGTCTCTCTTGTGCAGCAAGCGG
TTTCACGTTCACCAACTACGGTATCCACTGGATTCGTCAGGCACCAGGTAAAGGTCTGGAATGGGTAGCCTCTATCT
CTCCGTCTGGTGGTCTGACGTACTACCGTGACTCTGTCAAAGGTCGTTTCACCATCTCTCGTGATGACGCGAAAAAC
TCTCCGTACCTGCAGATGAACTCTCTGCGTGCAGAAGATACCGCAGTGTACTACTGCGCTACTGGTGGTGAAGGTAT
CTTCGACTACTGGGGTCAGGGTACCCTGGTAACTGTCTCAAGCGCTTCTACAAAGGGCCCATCGGTCTTCCCCCTGG
CACCCTCCTCCAAGAGCACCTCTGGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCTGTCCTACAGTCCTCTGGACTCTA
CTCCCTCAGCAGCGTGGTGACCGTGCCCTCCAGCAGCTTGGGCACCCAGACCTACATCTGCAACGTGAATCACAAGC
CCAGCAACACCAAGGTGGACAAGAAAGTTGAGCCCAAATCTTGTTCCGGAGGTGGCGGTTCCGGAGGTGGCGGTACC
GGTGGCGGTGGATCCGAAGTCCAGCTGCTTGAATCCGGAGGCGGACTCGTGCAGCCCGGAGGCAGTCTTCGCTTGTC
CTGCGCTGTATCTGGAATCGACCTGAGCAATTACGCCATCAACTGGGTGACACAGGCACCTGGGAAATGCCTCGAAT
GGATCGGCATTATATGGGCTAGTGGCACCACCTTTTATGCTACATGGGCGAAGGGTAGATTCACAATCTCACGGGAT
AATAGTAAGAACACAGTGTACCTGCAGATGAACTCCCTGCGAGCAGAGGATACCGCCGTTTACTATTGTGCTCGCAC
TGTCCCAGGTTATAGCACTGCACCCTACTTTGATCTGTGGGGCAGGGCACTCTGGTCACCGTCTCGAGTTGA

Fig. 8A

DNA encoding Light chain A26-645(gL4) including B72.3 leader sequence (SEQ ID NO:27)

ATGTCAGTTCCACACAGGTGCTGGGCTGCTTCTGTTGTGGCTCACCGATCCTAGGTGTGATATCCAGATGACCCA
GAGTCCAAGCAGTCTCTCCGCCAGCGTAGGCGATCGTGTGACTATTACCTGTCGTGCAACCCAGAGCATCTACAACG
CTCTGGCTTGGTATCAGCAGAAACCGGGTAAAGCGCCAAAACTCCTGATCTACAACGCGAACACTCTGCATACCGGT
GTTCCGTCTCGTTTCTCTGCGTCTGGTTCTGGTACGGACTCTACTCTGACCATCTCCTCTCTGCAGCCGGAAGATTT
CGCGACCTACTACTGCCAGCAGTACTACGATTACCCACTGACGTTTGGTGGTGGTACCAAAGTTGAGATCAAACGTA
CGGTGGCTGCACCATCTGTCTTCATCTTCCCCCCATCTGATGAGCAGTTGAAGTCTGGCACTGCCTCTGTTGTGTGC
CTGCTGAATAACTTCTACCCTAGAGAGGCCAAAGTCCAGTGGAAGGTGGATAACGCCCTTCAATCCGGAAACTCCCA
GGAGAGTGTCACTGAGCAGGACTCAAAGGACTCCACCTATAGCCTTAGCAGCACACTGACACTGAGCAAGGCTGACT
ACGAGAAACACAAGGTCTACGCCTGCGAAGTCACACATCAAGGCCTGAGCTCACCCGTGACAAAGAGCTTTAACAGG
GGAGAGTGTGGTGGAGGTGGCTCTGGCGGTGGTGGCTCCGGAGGCGGAGGAAGCGACATCCAGATGACCCAGAGCCC
TTCCTCTGTAAGCGCCAGTGTCGGAGACAGAGTGACTATTACCTGCCAAAGCTCCCCTTCAGTCTGGTCCAATTTTC
TATCCTGGTACCAGCAAAAGCCCGGAAAGGCTCCTAAATTGCTGATCTACGAAGCAAGCAAACTCACCAGCGGCGTG
CCCAGCAGGTTCAGCGGCAGTGGGTCTGGAACTGACTTTACCCTGACAATCTCCTCACTCCAGCCCGAGGACTTCGC
CACCTATTACTGCGGTGGAGGTTACAGTAGCATAAGTGATACGACATTTGGATGCGGCACTAAAGTGGAAATCAAGC
GTACCTGA

Fig. 8B

DNA encoding Light chain A26-645(gL4) (SEQ ID NO:28)

GATATCCAGATGACCCAGAGTCCAAGCAGTCTCTCCGCCAGCGTAGGCGATCGTGTGACTATTACCTGTCGTGCAAC
CCAGAGCATCTACAACGCTCTGGCTTGGTATCAGCAGAAACCGGGTAAAGCGCCAAAACTCCTGATCTACAACGCGA
ACACTCTGCATACCGGTGTTCCGTCTCGTTTCTCTGCGTCTGGTTCTGGTACGGACTCTACTCTGACCATCTCCTCT
CTGCAGCCGGAAGATTTCGCGACCTACTACTGCCAGCAGTACTACGATTACCCACTGACGTTTGGTGGTGGTACCAA
AGTTGAGATCAAACGTACGGTGGCTGCACCATCTGTCTTCATCTTCCCCCCATCTGATGAGCAGTTGAAGTCTGGCA
CTGCCTCTGTTGTGTGCCTGCTGAATAACTTCTACCCTAGAGAGGCCAAAGTCCAGTGGAAGGTGGATAACGCCCTT
CAATCCGGAAACTCCCAGGAGAGTGTCACTGAGCAGGACTCAAAGGACTCCACCTATAGCCTTAGCAGCACACTGAC
ACTGAGCAAGGCTGACTACGAGAAACACAAGGTCTACGCCTGCGAAGTCACACATCAAGGCCTGAGCTCACCCGTGA
CAAAGAGCTTTAACAGGGGAGAGTGTGGTGGAGGTGGCTCTGGCGGTGGTGGCTCCGGAGGCGGAGGAAGCGACATC
CAGATGACCCAGAGCCCTTCCTCTGTAAGCGCCAGTGTCGGAGACAGAGTGACTATTACCTGCCAAAGCTCCCCTTC
AGTCTGGTCCAATTTCTATCCTGGTACCAGCAAAAGCCCGGAAAGGCTCCTAAATTGCTGATCTACGAAGCAAGCA
AACTCACCAGCGGCGTGCCCAGCAGGTTCAGCGGCAGTGGGTCTGGAACTGACTTTACCCTGACAATCTCCTCACTC
CAGCCCGAGGACTTCGCCACCTATTACTGCGGTGGAGGTTACAGTAGCATAAGTGATACGACATTTGGATGCGGCAC
TAAAGTGGAAATCAAGCGTACCTGA

A26 Fab-Fv inhibits a human mixed lymphocyte reaction

A26 Fab-Fv inhibits IFN-γ production during a human MLR

A26 Fab-Fv administered prior to cell transfer dose dependently inhibits $CD4^+$ T cell proliferation in the Hu-NSG model A26 Fab-Fv administered prior to cell transfer dose dependently inhibits CD8$^+$ T cell proliferation in the Hu-NSG model A26 Fab-Fv administered prior to cell transfer dose dependently inhibits CD4$^+$ T cell proliferation in the Hu-NSG model A26 Fab-Fv administered prior to cell transfer dose dependently inhibits CD8+ T cell proliferation in the Hu-NSG model

METHOD OF TREATMENT WITH ANTIBODIES HAVING SPECIFICITY FOR HUMAN OX40

CROSS REFERENCE TO RELATED APPLICATIONS

This application is a division of U.S. application Ser. No. 13/672,077, filed Nov. 8, 2012; which claims priority to U.S. Provisional Application No. 61/558,545 filed Nov. 11, 2011, which are all incorporated herein by reference in their entireties.

The present invention relates to antibody molecules having specificity for antigenic determinants of OX40 and compositions comprising the same. The present invention also relates to the therapeutic uses of the antibody molecules, compositions and methods for producing said antibody molecules.

OX40 (also known as CD134, TNFRSF4, ACT35 or TXGP1L) is a member of the TNF receptor superfamily, which includes 4-1BB, CD27, CD30 and CD40. The extracellular ligand binding domain of OX40 is composed of 3 full cysteine-rich domains (CRDs) and a partial, fourth C-terminal CRD (Bodmer et al., 2002, Trends Biochem Sci, 27, 19-26).

The ligand for OX40 is OX40L and 3 copies of OX40 bind to the trimeric ligand to form the OX40-OX40L complex (Compaan and Hymowitz, 2006, Structure, 14, 1321-1330). OX40 is a membrane-bound receptor; however a soluble isoform has also been detected (Taylor and Schwarz, 2001, J. Immunol. Methods, 255, 67-72). The functional significance of the soluble form is presently unknown. OX40 is not expressed on resting T cells, but is transiently expressed on activated T cells after ligation of the T cell receptor (TCR). The ligand for OX40, OX40L, is a member of the TNF family and is expressed on activated antigen presenting cells (APC), including B cells, macrophages, endothelial cells and dendritic cells (DC).

OX40 is a major costimulatory receptor with sequential engagement of CD28 and OX40 being required for optimal T cell proliferation and survival. Ligation of OX40 on activated T cells leads to enhanced cytokine production and proliferation of both CD4+ and CD8+ T cells (Gramaglia et al., 2000, J. Immunol., 165, 3043-3050, Bansal-Pakala et al., 2004, J. Immunol, 172, 4821-425) and can contribute to both ongoing Th1 and Th2 responses (Gramaglia et al., 1998, J. Immuno., 161, 6510-6517, Arestides et al., 2002, Eur. J. Immunol. 32, 2874-2880). OX40 costimulation prolongs T cell survival beyond the initial effector phase of the immune response and increases the number of memory T cells through inhibition of effector T cell death.

When immune activation is excessive or uncontrolled, pathological allergy, asthma, inflammation, autoimmune and other related diseases may occur. Because OX40 functions to enhance immune responses, it may exacerbate autoimmune and inflammatory diseases.

The role of OX40/OX40L interactions in models of disease has been demonstrated in OX40 knockout mice. In experimental allergic encephalomyelitis (EAE), a model of multiple sclerosis, less severe clinical signs of disease and reduced inflammatory infiltrate within the CNS was noted in OX40 knockout mice (Carboni et al., 2003, J. Neuroimmunology, 145, 1-11). Also OX40 knockout mice primed and challenged with ovalbumin exhibit diminished lung inflammation (80-90% reduction in eosinophilia), reduced mucus production, and significantly attenuated airway hyper-reactivity (Jember et al., 2001, J. Exp. Med., 193, 387-392). Monoclonal antibodies to murine OX40 ligand have shown beneficial effects in the collagen-induced arthritis model of rheumatoid arthritis (Yoshioka et al., 2000, Eur. J. Immunol., 30, 2815-2823), EAE (Nohara et al., 2001, J. Immunol., 166, 2108-2115), non-obese diabetic (NOD) mice (Pakala et al., 2004, Eur. J. Immunol., 34, 3039-3046), colitis in T cell restored mice (Malmstrom et al., 2001, J. Immunol., 166, 6972-6981, Totsuka et al., 2003, Am. J. Physiol. Gastrointest. Liver Physiol., 284, G595-G603) and models of lung inflammation (Salek-Ardakani et al., 2003, J. Exp. Med., 198, 315-324, Hoshino et al., 2003, Eur J. Immunol, 33, 861-869). An antibody to human OX40L has been profiled in a model of lung inflammation in rhesus monkeys and resulted in reduced levels of IL-5, IL-13 and effector memory T cells in bronchiolar lavage fluid after allergen challenge (Seshasayee et al., 2007, J. Clin. Invest, 117, 3868-3878).

An increase in the expression of OX40 has been noted in several autoimmune and inflammatory diseases. This includes an increase in OX40 expression on T cells isolated from the synovial fluid of rheumatoid arthritis patients (Brugnoni D et al., 1998, Br. J. Rheum., 37, 584-585; Yoshioka et al., 2000, Eur. J. Immunol., 30, 2815-2823; Giacomelli R et al., 2001, Clin. Exp. Rheumatol., 19, 317-320). Similarly an increase in OX40 expression has been noted in gastrointestinal tissue from patients with ulcerative colitis and Crohn's disease (Souza et al., 1999, Gut, 45, 856-863; Stuber et al., 2000, Eur. J. Clin. Invest., 30, 594-599) and in active lesions of patients with multiple sclerosis (Carboni et al., 2003, J. Neuroimmunology, 145, 1-11). OX40L can also be detected on human airway smooth muscle (ASM) and asthma patients ASM cells show greater inflammatory responses to OX40L ligation than healthy donors, indicating a role for the OX40/OX40L pathway in asthma (Burgess et al., 2004, J. Allergy Clin Immunol., 113, 683-689; Burgess et al., 2005, J. Allergy Clin Immunol., 115, 302-308). It has also been reported that CD4+ T cells isolated from the peripheral blood of systemic lupus erythematosus (SLE) patients express elevated levels of OX40 which is associated with disease activity (Patschan et al., 2006, Clin. Exp. Immunol., 145, 235-242).

Given the role of OX40 in allergy, asthma and diseases associated with autoimmunity and inflammation, one approach to therapy in these diseases is to block OX40-OX40L signalling through the use of anti-OX40L antibodies or antagonistic anti-OX40 antibodies Anti-OX40L antibodies have been described, see for example WO2006/029879. Numerous agonistic anti-OX40 antibodies have been described but very few antagonistic anti-OX40 antibodies are known. A rabbit polyclonal anti-mouse OX40 antibody was produced by Stuber et al., 1996, J. Exp. Med, 183, 979-989 which blocks the interaction between OX40 and OX40L. Mouse monoclonal antibodies, 131 and 315 which bind human OX40 were generated by Imura et al., 1996, J. Exp. Med, 2185-2195.

Fully human antagonistic antibodies have been described in WO2007/062245, the highest affinity of these antibodies had an affinity for cell surface expressed OX40 (activated T cells) of 11 nM.

Humanised antagonistic antibodies have been described in WO2008/106116 and the antibody with the best affinity for OX40 had an affinity of 0.94 nM.

Other anti-OX40 antibodies have been described, including murine L106 (U.S. Pat. No. 6,277,962) and murine ACT35, commercially available from eBioscience.

We have previously described high affinity antagonistic anti-OX40 antibodies in International Patent application number WO2010/096418.

We have also previously described in International Patent application number WO2010/035012, a novel multi-specific antibody fusion molecule, hereinafter referred to as a Fab-dsFv and illustrated herein in FIG. 1. The same application provides useful anti-albumin binding variable regions which may be used to extend the half-life of the molecule.

In the present invention these albumin binding variable regions have been improved and combined in the Fab-dsFv format with the anti-OX40 antibodies described in WO2010/096418. The new bispecific molecule of the present invention has improved efficacy in a number of in vitro and in vivo assays described herein when compared to the Fab'-PEG molecule previously described in WO2010/096418. Accordingly, the present invention provides a bispecific antibody fusion protein which binds both human OX40 and human serum albumin which is suitable for use in the treatment or prophylaxis of pathological disorders mediated by OX40 or associated with an increased level of OX40.

BRIEF DESCRIPTION OF THE DRAWINGS

FIG. 2A) Light chain V region of antibody A26 (SEQ ID NO:7)

FIG. 2B) Heavy chain V region of antibody A26 (SEQ ID NO:8)

FIG. 2C) CDRH1 (SEQ ID NO:1), CDRH2 (SEQ ID NO:2), CDRH3 (SEQ ID NO:3), CDRL1 (SEQ ID NO:4), CDRL2 (SEQ ID NO:5) and CDRL3 (SEQ ID NO:6) of antibody A26.

FIG. 2D) Light chain of antibody A26 Fab component (SEQ ID NO:9)

FIG. 2E) Heavy chain of antibody A26 Fab component (SEQ ID NO:10)

FIG. 3A) Heavy chain of anti-albumin Fv component 645gH5 (SEQ ID NO:11)

FIG. 3B) Light chain of anti-albumin Fv component 645gL4 (SEQ ID NO:12)

FIG. 3C) Linker 1 (SEQ ID NO:13)

FIG. 3D) Linker 2 (SEQ ID NO:14)

FIG. 3E) Fab-dsFv heavy chain (SEQ ID NO:15)

FIG. 3F) Fab-dsFv light chain (SEQ ID NO:16)

FIG. 4A) 645g1 heavy chain variable domain (SEQ ID NO:17)

FIG. 4B) 645g1 light chain variable domain (SEQ ID NO:18)

FIG. 4C) A26 Fab-dsFv 645gH1 (SEQ ID NO:19)

FIG. 4D) A26 Fab-dsFv 645gL1 (SEQ ID NO:20)

FIG. 5A) DNA encoding heavy chain of the Fab-dsFv including OmpA leader (SEQ ID NO:21)

FIG. 5B) DNA encoding heavy chain of the Fab-dsFv without OmpA leader (SEQ ID NO:22)

FIG. 6A) DNA encoding light chain of the Fab-dsFv including OmpA leader (SEQ ID NO:23)

FIG. 6B) DNA encoding light chain of the Fab-dsFv without OmpA leader (SEQ ID NO:24)

FIG. 7A) DNA encoding heavy chain of the Fab-dsFv including B72.3 leader (SEQ ID NO:25)

FIG. 7B) DNA encoding heavy chain of the Fab-dsFv without B72.3 leader (SEQ ID NO:26)

FIG. 8A) DNA encoding light chain of the Fab-dsFv including B72.3 leader (SEQ ID NO:27)

FIG. 8B) DNA encoding light chain of the Fab-dsFv without B72.3 leader (SEQ ID NO:28)

Humanised CA044_00026 anti-OX40 antibody, is referred to herein as A26.

Figure 1:
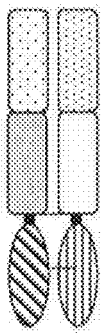
FIG. 1 shows a bispecific antibody fusion of the present invention (Fab-dsFv format)

The antibody fusion molecule of the present invention, referred to herein as a Fab-dsFv, is illustrated in FIG. 1. In the present invention the Fab portion (comprising the first heavy and light chain variable regions and the constant domains) binds human OX40 and the dsFv portion (comprising the second heavy and light chain variable regions, linked by a disulphide bond) binds human serum albumin. In particular, the Fab portion comprises the CDRs derived from an antagonistic anti-OX40 antibody and the Fv portion comprises the heavy and light chain variable regions of a humanised anti-albumin antibody, and these albumin binding variable regions are linked by a disulphide bond.

Accordingly, the present invention provides a bispecific antibody fusion protein which binds human OX40 and human serum albumin comprising:

a heavy chain comprising, in sequence from the N-terminal, a first heavy chain variable domain ($V_H1$), a CH1 domain and a second heavy chain variable domain ($V_H2$), a light chain comprising, in sequence from the N-terminal, a first light chain variable domain ($V_L1$), a CL domain and a second light chain variable domain ($V_L2$), wherein said heavy and light chains are aligned such that $V_H1$ and $V_L1$ form a first antigen binding site and $V_H2$ and $V_L2$ form a second antigen binding site, wherein the antigen bound by the first antigen binding site is human OX40 and the antigen bound by the second antigen binding site is human serum albumin, in particular wherein the first variable domain of the heavy chain ($V_H1$) comprises the sequence given in SEQ ID NO:1 for CDR-H1, the sequence given in SEQ ID NO:2 for CDR-H2 and the sequence given in SEQ ID NO:3 for CDR-H3 and the first variable domain of the light chain ($V_L1$) comprises the sequence given in SEQ ID NO:4 for CDR-L1, the sequence given in SEQ ID NO:5 for CDR-L2 and the sequence given in SEQ ID NO:6 for CDR-L3, wherein the second heavy chain variable domain ($V_H2$) has the sequence given in SEQ ID NO:11 and the second light chain variable domain ($V_L2$) has the sequence given in SEQ ID NO: 12 and the second heavy chain variable domain ($V_H2$) and second light chain variable domain ($V_L2$) are linked by a disulphide bond.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

The bispecific fusion protein of the present invention comprises a Fab fragment of the anti-OX40 antagonistic antibody previously described in WO2010/096418. As used herein, the term 'antagonistic' describes an antibody fusion protein that is capable of inhibiting and/or neutralising the biological signalling activity of OX40, for example by blocking binding or substantially reducing binding of OX40 to OX40 ligand and thus inhibiting the activation of OX40.

Screening for antibodies to identify those that bind OX40 can be performed using assays to measure binding to human OX40 and/or assays to measure the ability to block the binding of OX40 to its ligand, OX40L. An example of a binding assay is an ELISA, in particular, using a fusion protein of human OX40 and human Fc, which is immobilized on plates, and employing a conjugated secondary antibody to detect anti-OX40 antibody bound to the fusion protein. An example of a blocking assay is a flow cytometry based assay measuring the blocking of OX40 ligand fusion protein binding to OX40 on human CD4 cells. A fluorescently labelled secondary antibody is used to detect the amount of OX40 ligand fusion protein binding to the cell. This assay is looking for a reduction in signal as the antibody in the supernatant blocks the binding of ligand fusion protein to OX40. A further example of a blocking assay is an assay where the blocking of costimulation of naive human T cells mediated by OX40 ligand fusion protein coated to a plate is measured by measuring tritiated thymidine incorporation.

In the present invention, the variable regions are humanised. Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585, 089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

In the present invention the CDRs of $V_H1$ and $V_L1$ are derived from the antibody known as A26, described in WO2010/096418. Accordingly, in the bispecific antibody fusion protein of the present invention, the first variable domain of the heavy chain ($V_H1$) comprises the sequence given in SEQ ID NO:1 for CDR-H1, the sequence given in SEQ ID NO:2 or SEQ ID NO:23 for CDR-H2 and the sequence given in SEQ ID NO:3 for CDR-H3 and the first variable domain of the light chain ($V_L1$) comprises the sequence given in SEQ ID NO:4 or SEQ ID NO:24 for CDR-L1, the sequence given in SEQ ID NO:5 for CDR-L2 and the sequence given in SEQ ID NO:6 for CDR-L3.

It will be appreciated that one or more amino acid substitutions, additions and/or deletions may be made to the CDRs provided by the present invention without significantly altering the ability of the antibody to bind to OX40 and to neutralise OX40 activity. The effect of any amino acid substitutions, additions and/or deletions can be readily tested by one skilled in the art, for example by using the methods described in WO2010/096418, to determine OX40 binding and inhibition of the OX40/OX40L interaction. Accordingly, the present invention provides a bispecific antibody having specificity for human OX40 comprising CDRH-1 (SEQ ID NO:1), CDRH-2 (SEQ ID NO:2), CDRH-3 (SEQ ID NO:3), CDRL-1 (SEQ ID NO:4), CDRL-2 (SEQ ID NO:5) and CDRL-3 (SEQ ID NO:6) as shown in FIG. 2C, for example in which one or more amino acids, for example 1 or 2 amino acids, in one or more of the CDRs has been substituted with another amino acid, such as a similar amino acid as defined herein below.

In one embodiment, a bispecific antibody fusion protein of the present invention comprises a heavy chain, wherein the first variable domain of the heavy chain comprises three CDRs wherein the sequence of CDRH-1 has at least 90% identity or similarity to the sequence given in SEQ ID NO:1, CDRH-2 has at least 90% identity or similarity to the sequence given in SEQ ID NO:2 and/or CDRH-3 has at least 90% identity or similarity to the sequence given in SEQ ID NO:3. In another embodiment, a bispecific antibody fusion protein of the present invention comprises a heavy chain, wherein the variable domain of the heavy chain comprises three CDRs wherein the sequence of CDRH-1 has at least 95% or 98% identity or similarity to the sequence given in SEQ ID NO:1, CDRH-2 has at least 95% or 98% identity or similarity to the sequence given in SEQ ID NO:2 and/or CDRH-3 has at least 95% or 98% identity or similarity to the sequence given in SEQ ID NO:3.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

In another embodiment, a bispecific antibody fusion protein of the present invention comprises a light chain, wherein the first variable domain of the light chain comprises three CDRs wherein the sequence of CDRL-1 has at least 90% identity or similarity to the sequence given in SEQ ID NO:4, CDRL-2 has at least 90% identity or similarity to the sequence given in SEQ ID NO:5 and/or CDRL-3 has at least 90% identity or similarity to the sequence given in SEQ ID NO:6. In another embodiment, a bispecific antibody fusion protein of the present invention comprises a light chain, wherein the first variable domain of the light chain comprises three CDRs wherein the sequence of CDRL-1 has at least 95% or 98% identity or similarity to the sequence given in SEQ ID NO:4, CDRL-2 has at least 95% or 98% identity or similarity to the sequence given in SEQ ID NO:5 and/or CDRL-3 has at least 95% or 98% identity or similarity to the sequence given in SEQ ID NO:6.

In one embodiment the Fab portion of the bispecific antibody fusion protein provided by the present invention is a humanised or CDR-grafted antibody molecule comprising one or more of the CDRs provided in SEQ ID NOs:1, 2, 3, 4, 5 and/or 6 (FIG. 2C or variants thereof. As used herein, the term 'CDR-grafted antibody molecule' refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the CDR-grafted antibody according to the present invention has a variable domain comprising human acceptor framework regions as well as one or more of the CDRs or specificity determining residues described above. Thus, provided in one embodiment is a neutralising CDR-grafted antibody wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.mrc-cpe.cam.ac.uk/

In a CDR-grafted antibody of the present invention, the acceptor heavy and light chains do not necessarily need to be derived from the same antibody and may, if desired, comprise composite chains having framework regions derived from different chains.

A suitable framework region for the first heavy chain variable domain (VH1) of the present invention is derived from the human sub-group VH3 sequence 1-3 3-07 together with JH4. A suitable framework region for the light chain for the first light chain variable domain (VL1) is derived from the human germline sub-group VK1 sequence 2-1 1-02 together with JK4.

Also, in a CDR-grafted antibody variable region of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

Suitably, in the first heavy chain variable region (VH1) of the present invention, if the acceptor heavy chain has the human VH3 sequence 1-3 3-07 together with JH4, then the acceptor framework regions of the heavy chain comprise, in addition to one or more donor CDRs, a donor residue at least one of positions 37, 73, 78 or 94 (according to Kabat et al., (supra)). Accordingly, provided is a bispecific antibody fusion protein, wherein at least the residues at positions 37, 73, 78 and 94 of the first variable domain of the heavy chain are donor residues.

Suitably, in the first light chain variable region (VL1) of the present invention, if the acceptor light chain has the human sub-group VK1 sequence 2-1 1-02 together with JK4, then the acceptor framework regions of the light chain comprise, in addition to one or more donor CDRs, a donor residue at least one of positions 64 or 71. Accordingly, provided is a bispecific antibody fusion protein wherein at least the residues at positions 64 and 71 of the first variable domain of the light chain are donor residues.

Donor residues are residues from the donor antibody, i.e. the antibody from which the CDRs were originally derived.

In one embodiment, a bispecific antibody fusion protein of the present invention comprises a heavy chain, wherein the first variable domain of the heavy chain ($V_H1$) comprises the sequence given in FIG. 2B SEQ ID NO:8.

It will be appreciated that one or more amino acid, for example 1 or 2 amino acid, substitutions, additions and/or deletions may be made to the first heavy and light chain variable domains, provided by the present invention, without significantly altering the ability of the antibody fusion protein to bind to OX40 and to neutralise OX40 activity. The effect of any amino acid substitutions, additions and/or deletions can be readily tested by one skilled in the art, for example by using the methods described in WO2010/096418, to determine OX40 binding and ligand blocking.

In one embodiment, a bispecific antibody fusion protein of the present invention comprises a heavy chain, wherein the first variable domain of the heavy chain comprises a sequence having at least 60% identity or similarity to the sequence given in FIG. 2B SEQ ID NO:8. In one embodiment, an antibody fusion protein of the present invention comprises a heavy chain (VH1), wherein the first variable domain of the heavy chain comprises a sequence having at least 70%, 80%, 90%, 95% or 98% identity or similarity to the sequence given in SEQ ID NO:8.

In one embodiment, a bispecific antibody fusion protein of the present invention comprises a light chain, wherein the first variable domain of the light chain (VL1) comprises the sequence given in FIG. 2A SEQ ID NO:7.

In another embodiment, a bispecific antibody fusion protein of the present invention comprises a light chain, wherein the first variable domain of the light chain comprises a sequence having at least 60% identity or similarity to the sequence given in SEQ ID NO:7. In one embodiment the antibody fusion protein of the present invention comprises a light chain, wherein the first variable domain of the light chain comprises a sequence having at least 70%, 80%, 90%, 95% or 98% identity or similarity to the sequence given in SEQ ID NO: 7.

In one embodiment a bispecific antibody fusion protein of the present invention comprises a heavy chain, wherein the first variable domain of the heavy chain (VH1) comprises the sequence given in SEQ ID NO:8 and a light chain, wherein the first variable domain of the light chain (VL1) comprises the sequence given in SEQ ID NO:7.

In another embodiment of the invention, the antibody fusion protein comprises a heavy chain and a light chain, wherein the first variable domain of the heavy chain comprises a sequence having at least 60% identity or similarity to the sequence given in SEQ ID NO:8 and the first variable domain of the light chain comprises a sequence having at least 60% identity or similarity to the sequence given in SEQ ID NO:7. Suitably, the antibody fusion protein comprises a heavy chain, wherein the first variable domain of the heavy chain comprises a sequence having at least 70%, 80%, 90%, 95% or 98% identity or similarity to the sequence given in SEQ ID NO:8 and a light chain, wherein the first variable domain of the light chain comprises a sequence having at least 70%, 80%, 90%, 95% or 98% identity or similarity to the sequence given in SEQ ID NO:7.

In the bispecific antibody fusion protein of the present invention the heavy chain comprises a CH1 domain and light chain comprises a CL domain, either kappa or lambda.

In one embodiment a bispecific antibody fusion protein of the present invention comprises a heavy chain, wherein the heavy chain comprises the sequence given in SEQ ID NO:10 and a light chain, wherein the light chain comprises the sequence given in SEQ ID NO:9.

It will be appreciated that one or more amino acid, for example 1 or 2 amino acid, substitutions, additions and/or deletions may be made to the antibody variable and/or constant domains provided by the present invention without significantly altering the ability of the antibody to bind to OX40 and to neutralise OX40 activity. The effect of any amino acid substitutions, additions and/or deletions can be readily tested by one skilled in the art, for example by using the methods described in WO2010096418, to determine OX40 binding and blocking of the OX40/OX40L interaction.

In one embodiment of the invention, the antibody fusion protein comprises a heavy chain, wherein the VH1 and CH1 domains of heavy chain comprise a sequence having at least 60% identity or similarity to the sequence given in SEQ ID NO:10. Suitably, the antibody fusion comprises a heavy chain, wherein the VH1 and CH1 domains of the heavy chain comprise a sequence having at least 70%, 80%, 90%, 95% or 98% identity or similarity to the sequence given in SEQ ID NO:10.

In one embodiment a bispecific antibody fusion molecule according to the present invention comprises a light chain comprising the sequence given in FIG. 2D, SEQ ID NO:9.

In one embodiment of the invention, the antibody fusion protein comprises a light chain, wherein the $V_L1$ and the CH1 domains of the light chain comprise a sequence having at least 60% identity or similarity to the sequence given in SEQ ID NO:9. For example, the antibody fusion protein comprises a light chain, wherein the VL1 and CL domains of the light chain comprise a sequence having at least 70%, 80%, 90%, 95% or 98% identity or similarity to the sequence given in SEQ ID NO:9.

The second antigen bound by the bispecific antibody fusion protein of the present invention is human serum albumin. This is bound by the Fv portion of the Fab-dsFv which is made up of the second heavy and light chain variable domains, $V_H2$ and $V_L2$. In the present invention, $V_H2$ and $V_L2$ are derived from one of the antibodies described in WO2010/035012 and represent an improved, more human graft of that antibody.

In one embodiment the second heavy chain variable domain ($V_H2$) has the sequence given in FIG. 3A SEQ ID NO:11.

In one embodiment the second light chain variable domain ($V_L2$) has the sequence given in FIG. 3B SEQ ID NO:12.

Accordingly, the present invention provides a bispecific antibody fusion protein which binds human OX40 and human serum albumin comprising:

a heavy chain comprising, in sequence from the N-terminal, a first heavy chain variable domain ($V_H1$), a CH1 domain and a second heavy chain variable domain ($V_H2$), a light chain comprising, in sequence from the N-terminal, a first light chain variable domain ($V_L1$), a CL domain and a second light chain variable domain ($V_L2$), wherein said heavy and light chains are aligned such that $V_H1$ and $V_L1$ form a first antigen binding site and $V_H2$ and $V_L2$ form a second antigen binding site, wherein the antigen bound by the first antigen binding site is human OX40 and the antigen bound by the second antigen binding site is human serum albumin, wherein the first variable domain of the heavy chain ($V_H1$) comprises the sequence given in SEQ ID NO:1 for CDR-H1, the sequence given in SEQ ID NO:2 for CDR-H2 and the sequence given in SEQ ID NO:3 for CDR-H3 and the first variable domain of the light chain ($V_L1$) comprises the sequence given in SEQ ID NO:4 for CDR-L1, the sequence given in SEQ ID NO:5 for CDR-L2 and the sequence given in SEQ ID NO:6 for CDR-L3, wherein the second heavy chain variable domain ($V_H2$) has the sequence given in SEQ ID NO:11 and the second light chain variable domain ($V_L2$) has the sequence given in SEQ ID NO: 12 and the second heavy chain variable domain ($V_H2$) and second light chain variable domain ($V_L2$) are linked by a disulphide bond.

Preferably the CH1 domain and the second heavy chain variable domain ($V_H2$) are connected via a linker and the CL domain and the second light chain variable domain ($V_L2$) are connected via linker. Any suitable peptide linker sequence may be used and these may be the same in each chain or different. Suitable linkers have previously been described in WO2010/035012 and are incorporated herein by reference. Examples of suitable linkers are shown in FIGS. 3C and 3D. In one embodiment the linker between the CH1 domain and the second heavy chain variable domain ($V_H2$) comprises or consists of the sequence given in FIG. 3C SEQ ID NO:13. In one embodiment the linker between the CH1 domain and the second heavy chain variable domain ($V_H2$) comprises or consists of the sequence given in FIG. 3C SEQ ID NO:14. In one embodiment the linker between the CL domain and the second light chain variable domain ($V_L2$) comprises or consists of the sequence given in FIG. 3D SEQ ID NO:14.

In one embodiment the linker in the light chain is a 15 amino acid sequence, in particular GGGGSGGGGSGGGGS (SEQ ID NO: 29).

In one embodiment the linker in the heavy chain is a 16 amino acid sequence, in particular SGGGGSGGGGTGGGGS (SEQ ID NO: 30).

In one embodiment the present invention provides a bispecific antibody fusion protein in which the heavy chain comprises or consists of the sequence given in FIG. 3E (SEQ ID NO:15) and the light chain comprises or consists of the sequence given in FIG. 3F (SEQ ID NO:16).

In one embodiment of the invention, the bispecific antibody fusion protein comprises a heavy chain and a light chain, wherein the heavy chain comprises a sequence having at least 60% identity or similarity to the sequence given in SEQ ID NO:15 and the light chain comprises a sequence having at least 60% identity or similarity to the sequence given in SEQ ID NO:16. Generally, the antibody fusion comprises a heavy chain, wherein the heavy chain comprises a sequence having at least 70%, 80%, 90%, 95% or 98% identity or similarity to the sequence given in SEQ ID NO:15 and a light chain, wherein the light chain comprises a sequence having at least 70%, 80%, 90%, 95% or 98% identity or similarity to the sequence given in SEQ ID NO:16.

The antibody fusion molecules of the present invention suitably have a high binding affinity, in particular picomolar affinity for human OX40 and nanomolar affinity for human serum albumin. Affinity may be measured using any suitable method known in the art, including Surface Plasmon Resonance e.g. BIAcore™, as described for OX40 in WO2010096418 and serum albumin in WO2010/035012, using isolated natural or recombinant OX40 or serum albumin or a suitable fusion protein/polypeptide.

In one example affinity is measured using recombinant human OX40 extracellular domain as described in WO2010/096418. In one example the recombinant human OX40 extracellular domain used is a dimer, for example an Fc fusion dimer. Suitably the antibody fusion molecules of the present invention have a binding affinity for isolated human OX40 of about 200 pM or less. In one embodiment the antibody molecule of the present invention has a binding affinity of about 100 pM or less. In one embodiment the antibody molecule of the present invention has a binding affinity of about 50 pM or less. In one embodiment the antibody fusion molecule of the present invention has a binding affinity of about 40 pM or less.

The antibody fusion molecules of the present invention suitably have a high binding affinity for human OX40 expressed on the surface of activated T cells, for example nanomolar or picomolar affinity. Affinity may be measured using any suitable method known in the art, including the method as described in WO2010096418 using activated $CD4^+$ $OX40^+$ human T cells. In particular the antibody fusion molecules of the present invention have a binding affinity for cell surface expressed human OX40 of about 2 nM or better. In one example the antibody molecules of the present invention have a binding affinity for cell surface expressed human OX40 of about 1 nM or better. In another example the antibody molecules of the present invention have a binding affinity for cell surface expressed human OX40 of about 0.5 nM or better. In another example the antibody molecules of the present invention have a binding affinity for cell surface expressed human OX40 of about 0.2 nM or better.

Suitably the antibody fusion molecules of the present invention have a binding affinity for isolated human serum albumin about 50 nM or less. Suitably the antibody fusion molecules of the present invention have a binding affinity for isolated human serum albumin of about 20 nM or less. In one embodiment the antibody molecule of the present invention has a binding affinity of about 10 nM or less. In one embodiment the antibody molecule of the present invention has a binding affinity of about 5 nM or less. In one embodiment the antibody fusion molecule of the present invention has a binding affinity of about 2 nM or less.

The antibody fusion molecules of the present invention can bind human serum albumin and cynomologous, mouse and rat serum albumin. In one embodiment the antibody fusion protein of the present invention bind cynomologus serum albumin with an affinity of 5 nM or less. In one embodiment the antibody fusion protein of the present invention binds mouse serum albumin with an affinity of 5 nM or less.

The antibody fusion molecules of the present invention are able to bind human OX40 and human serum albumin simultaneously.

Advantageously, the fusion molecules of the present invention have a high affinity for OX40 and also have a adequate half-life in vivo to be therapeutically useful, for example the half-life is in the range 5-15 days, such as 7-11 days.

It will be appreciated that the affinity of antibody fusion protein provided by the present invention for human OX40 and/or human serum albumin may be altered using any suitable method known in the art. The present invention therefore also relates to variants of the antibody molecules of the present invention, which have an improved affinity for OX40 or human serum albumin. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment the bispecific antibody fusion molecules of the present invention block the interaction between OX40 and OX40L. Numerous assays suitable for determining the ability of an antibody to block this interaction are described in WO2010/096418. In one embodiment the present invention provides an antibody fusion protein having specificity for human OX40 which is capable of inhibiting the binding of human OX40L (tested at a final concentration of 2 µg/ml) to activated human CD4+ OX40+ T cells by 50% at a concentration of less than 0.5 nM. In one embodiment the human OX40L used in the assay is natural human OX40. In one embodiment the human OX40 used in the assay is recombinant human OX40.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin. Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly (ethyleneglycol) such as methoxypoly(ethyleneglycol) or derivatives thereof.

Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da.

In one example suitable effector molecules may be attached through any available amino acid side-chain or terminal amino acid functional group located in the antibody fusion protein, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO98/25971).

The present invention also provides an isolated DNA sequence encoding the heavy and/or light chain(s) of an antibody molecule of the present invention. Suitably, the DNA sequence encodes the heavy or the light chain of an antibody molecule of the present invention. The DNA sequence of the present invention may comprise synthetic DNA, for instance produced by chemical processing, cDNA, genomic DNA or any combination thereof. DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable sequences are provided in FIG. 5A SEQ ID NO:21; FIG. 5B SEQ ID NO:22; FIG. 6A SEQ ID NO:23; FIG. 6B SEQ ID NO:24. Nucleotides 1-63 in SEQ ID NO 21 and 1-63 in SEQ ID NO:23 encode the signal peptide sequence OmpA which is cleaved to give an antagonistic antibody fusion molecule of the present invention. The present invention also provides an isolated DNA sequence encoding the heavy chain of an antibody fusion protein of the present invention which comprises SEQ ID NO:21 or SEQ ID NO:22. The present invention also provides an isolated DNA sequence encoding the light chain of an antibody fusion molecule of the present invention which comprises SEQ ID NO:23 or SEQ ID NO:24.

Other examples of suitable sequences are provided in FIG. 7A SEQ ID NO:25; FIG. 7B SEQ ID NO:26; FIG. 8A SEQ ID NO:27; FIG. 6B SEQ ID NO:28. Nucleotides 1-57 in SEQ ID NO 25 and 1-60 in SEQ ID NO 27 encode the signal peptide sequence from mouse antibody B72.3 (Whittle et al., 1987, Protein Eng. 1(6) 499-505) which is cleaved to give an antagonistic antibody fusion molecule of the present invention. The present invention also provides an isolated DNA sequence encoding the heavy chain of an antibody fusion protein of the present invention which comprises SEQ ID NO:25 or SEQ ID NO:26. The present invention also provides an isolated DNA sequence encoding the light chain of an antibody fusion molecule of the present invention which comprises SEQ ID NO:27 or SEQ ID NO:28.

The present invention also relates to a cloning or expression vector comprising one or more DNA sequences of the present invention. Accordingly, provided is a cloning or expression vector comprising one or more DNA sequences encoding an antibody fusion protein of the present invention. Suitably, the cloning or expression vector comprises two DNA sequences, encoding the light chain and the heavy chain of the antibody molecule of the present invention, respectively. Suitably, a vector according to the present invention comprises the sequences given in SEQ ID NO:21 and SEQ ID NO:23. Nucleotides 1-63 in SEQ ID NO 21 and 1-63 in SEQ ID NO 23 encode the signal peptide sequence from OmpA.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody fusion protein of the present invention. Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used. Suitable mammalian host cells include CHO, myeloma or hybridoma cells.

The present invention also provides a process for the production of an antibody fusion molecule according to the present invention comprising culturing a host cell containing a vector of the present invention under conditions suitable for leading to expression of protein from DNA encoding the antibody molecule of the present invention, and isolating the antibody molecule.

For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

As the antibody fusion proteins of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody fusion protein of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody fusion molecule of the present invention together with one or more of a pharmaceutically acceptable excipient, diluent or carrier.

The antibody fusion molecule may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies.

In a further embodiment the antibody fusion protein or composition according to the disclosure is employed in combination with a further pharmaceutically active agent, for example a corticosteroid (such as fluticasone propionate) and/or a beta-2-agonist (such as salbutamol, salmeterol or formoterol) or inhibitors of cell growth and proliferation (such as rapamycin, cyclophosphmide, methotrexate) or alternative a CD28 and/or CD40 inhibitor. In one embodiment the inhibitor is a small molecule. In another embodiment the inhibitor is an antibody specific to the target.

The pharmaceutical compositions suitably comprise a therapeutically effective amount of the antibody fusion protein of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, for example 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which the antibody fusion molecule of the present invention is administered depends on the nature of the condition to be treated, the extent of the inflammation present and on whether the antibody molecule is being used prophylactically or to treat an existing condition.

The frequency of dose will depend on the half-life of the antibody fusion molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody or fragment, for example if the pH of the formulation is 7 then a pI of from 8-9 or above may be appropriate. Whilst not wishing to be bound by theory it is thought that this may ultimately provide a final formulation with improved stability, for example the antibody or fragment remains in solution.

In one aspect advantageously the fusion molecule of the present disclosure does not have a pI which corresponds to an overall neutral molecule. This renders the molecule less susceptible to aggregation.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N. J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 µm, in particular from 1 to 5 µm. The particle size of the active ingredient (such as the antibody or fragment) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example a nebulizer connected to a compressor (e.g., the Pari LC-Jet Plus® nebulizer connected to a Pari Master® compressor manufactured by Pari Respiratory Equipment, Inc., Richmond, Va.).

The antibody fusion protein of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

The antibody fusion proteins disclosed herein may be suitable for delivery via nebulisation.

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides an antibody fusion molecule (or compositions comprising same) for use in the control of inflammatory diseases, for example acute or chronic inflammatory disease. Suitably, the antibody molecule (or compositions comprising same) can be used to reduce the inflammatory process or to prevent the inflammatory process. In one embodiment there is provided an in vivo reduction of activated T cells, in particular those involved in inappropriate inflammatory immune responses, for example recruited to the vicinity/location of such a response.

Reduction of activated T cells, as employed herein, may be a reduction, 10, 20, 30, 40, 50, 60, 70, 80, 90 or more percent in comparison to before treatment or without treatment. Advantageously, treatment with an antibody, fragment or composition according to the present invention, may allow the reduction in the level of activated T cells, without reducing the patients general level of T cells (unactivated T cells). This may result in fewer side effects, and possibly prevent T cell depletion in the patient.

The present invention also provides the antibody fusion molecule of the present invention for use in the treatment or prophylaxis of a pathological disorder that is mediated by OX40 or associated with an increased level of OX40. The pathological condition, may, for example be selected from the group consisting of infections (viral, bacterial, fungal and parasitic), endotoxic shock associated with infection, arthritis, rheumatoid arthritis, asthma, COPD, pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, arthritis, meningoencephalitis, autoimmune uveitis, immune mediated inflammatory disorders of the central and peripheral nervous system such as multiple sclerosis, lupus (such as systemic lupus erythematosus and lupus nephritis) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis and hypochlorhydia.

In one embodiment the antibody fusion protein according to the invention is employed in the treatment of allergy, COPD, autoimmune disease, rheumatoid arthritis, asthma, graft versus host disease, Crohn's disease, ulcerative colitis, type-1 diabetes, multiple sclerosis, Systemic lupus erythematosis, lupus nephritis, Myasthenia Gravis, Grave's disease, transplant rejection, Wegener's granulomatosis, Henoch-Schonlein purpura, systemic sclerosis or viral-induced lung inflammation.

In one embodiment the antibody fusion protein according to the invention is employed in the treatment of a disease selected from the group consisting of allergy, COPD, autoimmune disease, rheumatoid arthritis, asthma, graft versus host disease, Crohn's disease, ulcerative colitis, type-1 diabetes, multiple sclerosis, Systemic lupus erythematosis, lupus nephritis, Myasthenia Gravis, Grave's disease, transplant rejection, Wegener's granulomatosis, Henoch-Schonlein purpura, systemic sclerosis and viral-induced lung inflammation.

The present invention also provides an antibody fusion molecule according to the present invention for use in the treatment or prophylaxis of pain, particularly pain associated with inflammation.

In one embodiment the mechanism through which the fusion molecules of the present disclosure work include one or more of inhibition of T cell proliferations or survival, enhancement of TReg generation, reduced differentiation of B cells and/or decreased cytokine production.

The present invention further provides the use of an antibody fusion molecule or composition according to the present invention in the manufacture of a medicament for the treatment or prophylaxis of a pathological disorder that is mediated by OX40 or associated with an increased level of OX40, in particular the pathological disorder is rheumatoid arthritis, asthma or COPD.

The present invention further provides the use of an antibody molecule, fragment or composition according to the present invention in the manufacture of a medicament for the treatment or prophylaxis of one or more medical indications described herein.

An antibody fusion molecule or composition of the present invention may be utilised in any therapy where it is desired to reduce the effects of OX40 in the human or animal body. OX40 may be circulating in the body or may be present in an undesirably high level localised at a particular site in the body, for example a site of inflammation.

In one embodiment the antibody fusion molecule of the present invention or a composition comprising the same is used for the control of inflammatory disease, e.g. as described herein.

The present invention also provides a method of treating human or animal subjects suffering from or at risk of a disorder mediated by OX40, the method comprising administering to the subject an effective amount of the antibody fusion molecule of the present invention, or a composition comprising the same.

In one embodiment there is provided a purified bispecific antibody fusion protein which binds human OX40 and human serum albumin, in substantially purified from, in particular free or substantially free of endotoxin and/or host cell protein or DNA.

Purified form as used supra is intended to refer to at least 90% purity, such as 91, 92, 93, 94, 95, 96, 97, 98, 99% w/w or more pure.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 ng per mg of antibody product or less such as 100 ng per mg or less, in particular 20 ng per mg, as appropriate.

The antibody fusion molecule of the present invention may also be used in diagnosis, for example in the in vivo diagnosis and imaging of disease states involving OX40.

Advantageously, the present fusion molecules are thought to be safe for administration to humans at a proper therapeutic dose, in particular because they are not superagonists and are unlikely to cause cytokine storm.

Superagonist as employed herein refers to an antibody which expands T cells in the absence of TCR engagement.

In one embodiment A26 Fab-Fv reduces the Division Index indicating that fewer cells in the population are committed to division; this effect is presumably mediated by the NK cells that are expressing OX40. The Division Index represents the average number of cell divisions that a cell in the original population has undergone and includes the undivided cells.

The Proliferation Index reflects proliferation of the responding population only, and in one embodiment the inhibitory effect of A26 Fab-Fv using this measure is relatively reduced.

Comprising in the context of the present specification is intended to meaning including.

Where technically appropriate embodiments of the invention may be combined.

Embodiments are described herein as comprising certain features/elements. The disclosure also extends to separate embodiments consisting or consisting essentially of said features/elements.

The present invention is further described by way of illustration only in the following examples, which refer to the accompanying Figures, in which:

EXAMPLES

Figures in detail:
FIG. 1: A bispecific antibody fusion protein of the present invention, referred to as a Fab-dsFv.
FIG. 2A) Light chain V region of antibody A26 (SEQ ID NO:7)

FIG. 2B) Heavy chain V region of antibody A26 (SEQ ID NO:8)

FIG. 2C) CDRH1 (SEQ ID NO:1), CDRH2 (SEQ ID NO:2), CDRH3 (SEQ ID NO:3), CDRL1 (SEQ ID NO:4), CDRL2 (SEQ ID NO:5) and CDRL3 (SEQ ID NO:6) of antibody A26.

FIG. 2D) Light chain of antibody A26 Fab component (SEQ ID NO:9)

FIG. 2E) Heavy chain of antibody A26 Fab component (SEQ ID NO:10)

FIG. 3A) Heavy chain of anti-albumin Fv component 645gH5 (SEQ ID NO:11)

FIG. 3B) Light chain of anti-albumin Fv component 645gL4 (SEQ ID NO:12)

FIG. 3C) Linker 1 (SEQ ID NO:13)

FIG. 3D) Linker 2 (SEQ ID NO:14)

FIG. 3E) Fab-dsFv heavy chain (SEQ ID NO:15)

FIG. 3F) Fab-dsFv light chain (SEQ ID NO:16)

FIG. 4A) 645g1 heavy chain variable domain (SEQ ID NO:17)

FIG. 4B) 645g1 light chain variable domain (SEQ ID NO:18)

FIG. 4C) A26 Fab-dsFv 645gH1 (SEQ ID NO:19)

FIG. 4D) A26 Fab-dsFv 645gL1 (SEQ ID NO:20)

FIG. 5A) DNA encoding heavy chain of the Fab-dsFv including OmpA leader (SEQ ID NO:21)

FIG. 5B) DNA encoding heavy chain of the Fab-dsFv without OmpA leader (SEQ ID NO:22)

FIG. 6A) DNA encoding light chain of the Fab-dsFv including OmpA leader (SEQ ID NO:23)

FIG. 6B) DNA encoding light chain of the Fab-dsFv without OmpA leader (SEQ ID NO:24)

FIG. 7A) DNA encoding heavy chain of the Fab-dsFv including B72.3 leader (SEQ ID NO:25)

Figure 9A:
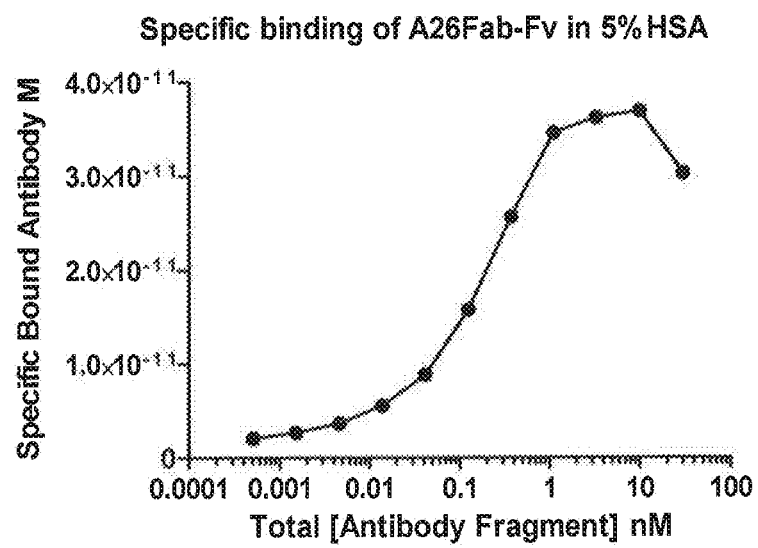
FIG. 9A shows binding of AlexaFluor 488 labelled A26 Fab-dsFv to activated human CD4$^+$ OX40$^+$ T cells
Figure 9B:
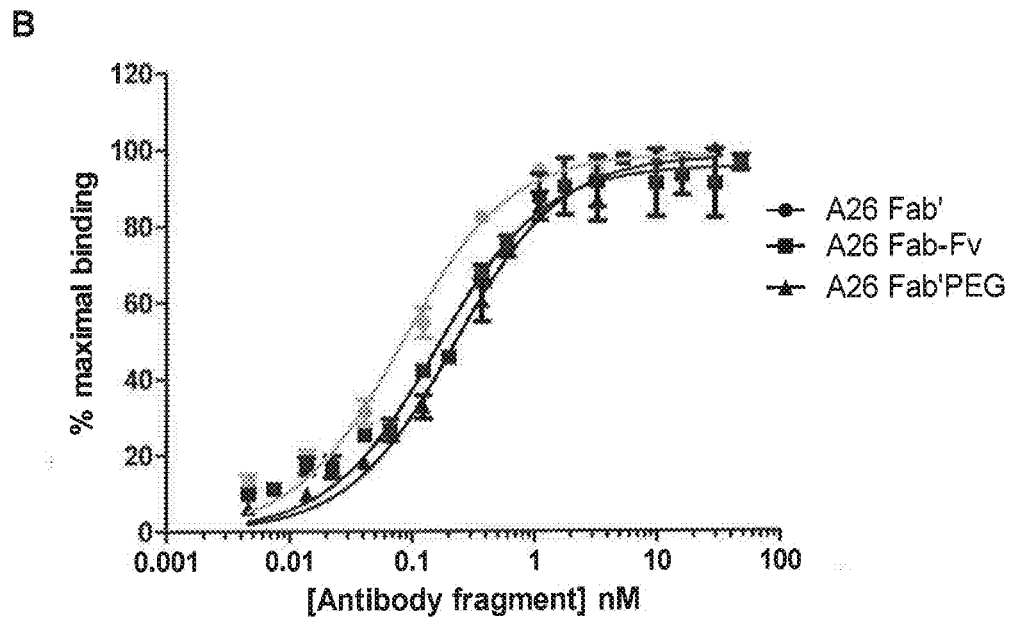
FIG. 9B shows binding for A26 Fab', A26 Fab-Fv and A26 Fab'-PEG in the presence of 5% HSA on activated human CD4+, OX40+ T cells.
Figure 10A:
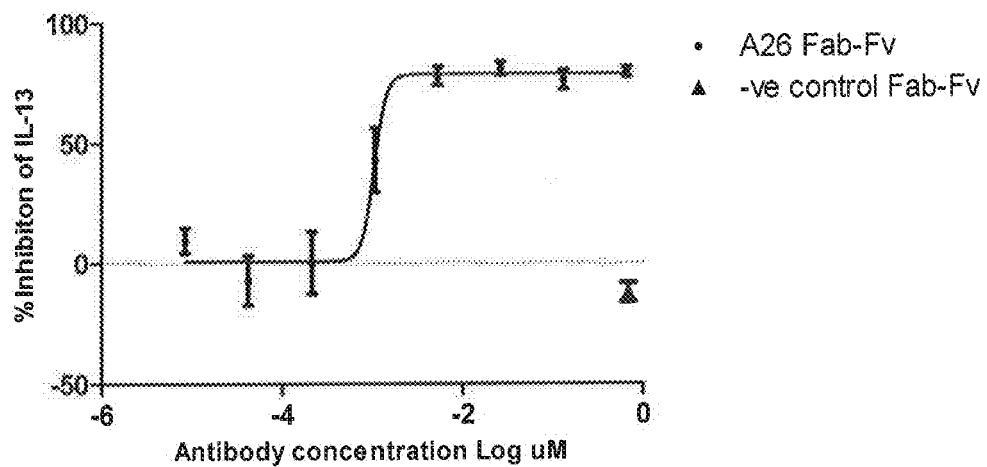
FIG. 10A shows the effect of A26 Fab-dsFv on cytokine production from PBMC exposed to *Dermatophagoides pteronyssinus* allergic extract
Figure 10B:
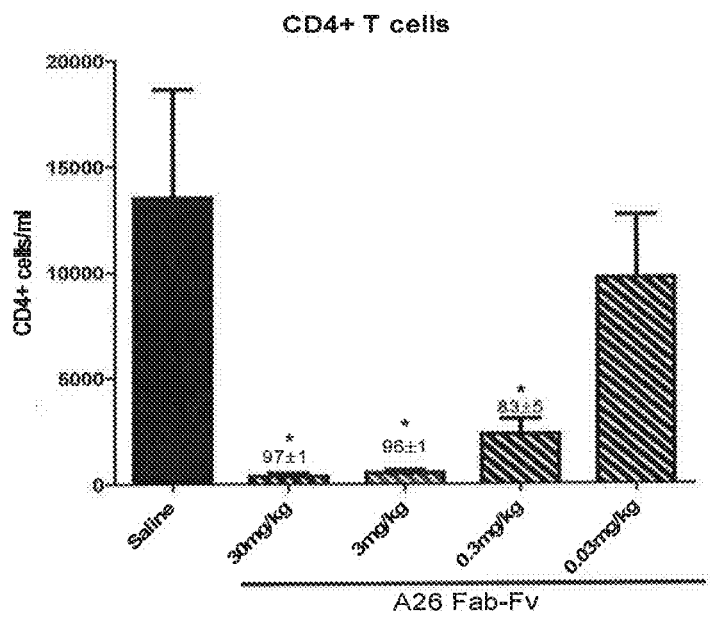
FIG. 10B shows the ability of A26 Fab-dsFv to inhibit CD4$^+$ and CD8$^+$ T cell proliferation in a Hu-NSG mouse model
Figure 11A:
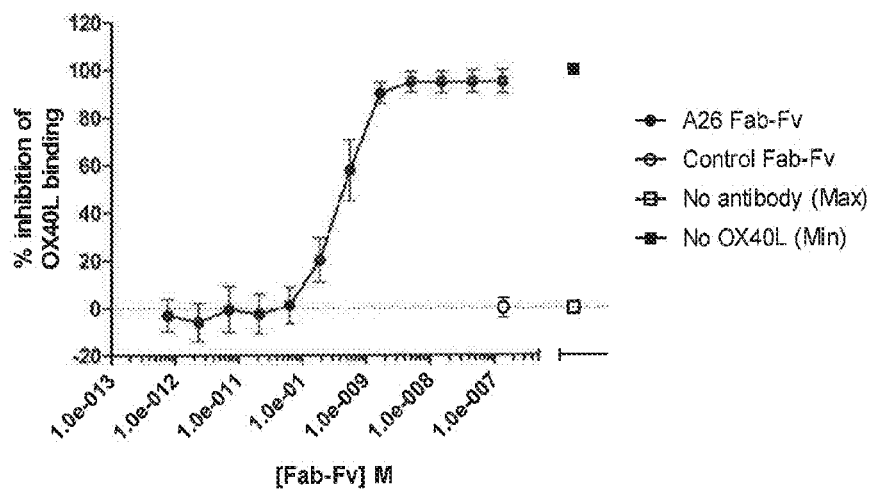
FIG. 11A shows inhibition of OX40L binding to human activated CD4$^+$ OX40$^+$ T cells by A26 Fab-dsFv
Figure 11B:
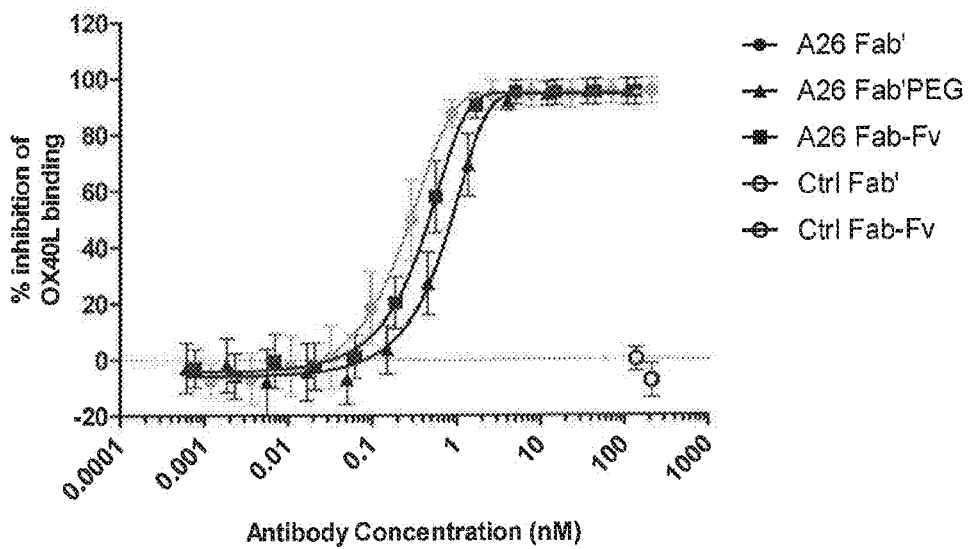
FIG. 11B shows inhibition of OX40L binding to human activated CD4$^+$ OX40$^+$ T cells by A26 Fab', A26 Fab-dsFv, A26 Fab'-PEG and two controls.

FIG. 7B) DNA encoding heavy chain of the Fab-dsFv without B72.3 leader (SEQ ID NO:26) CD4$^+$ OX40$^+$ T cells FIG. 9B shows binding for A26 Fab', A26 Fab-Fv and A26 Fab'-PEG in the presence of 5% HSA on activated human CD4+, OX40+ T cells FIG. 10A shows the effect of A26 Fab-dsFv on cytokine production from PBMC exposed to *Dermatophagoides pteronyssinus* allergic extract FIG. 10B shows the ability of A26 Fab-dsFv to inhibit CD4$^+$ and CD8$^+$ T cell proliferation in a Hu-NSG mouse model FIG. 11A shows inhibition of OX40L binding to human activated CD4$^+$ OX40$^+$ T cells by A26 Fab-dsFv FIG. 11B shows inhibition of OX40L binding to human activated CD4$^+$ OX40$^+$ T cells by A26 Fab', A26 Fab-dsFv, A26 Fab'-PEG and two controls.

Figure 12A:
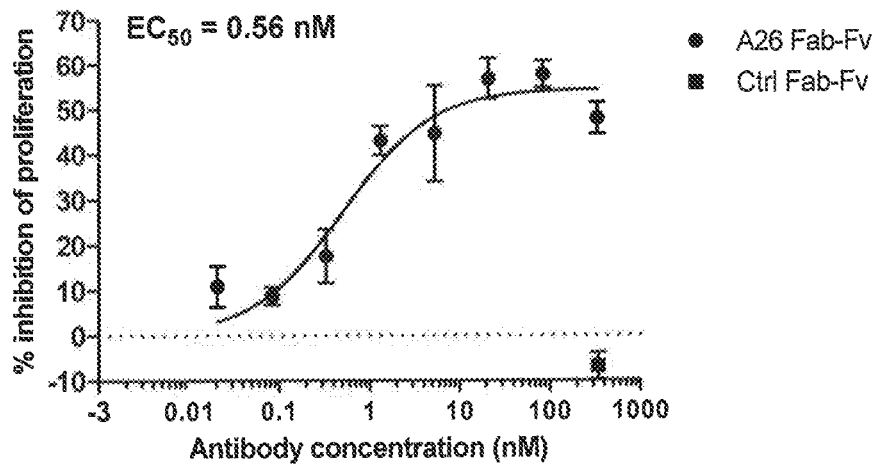
FIG. 12A shows A26 Fab-Fv inhibits a human mixed lymphocyte reaction (MLR)

FIG. 12A shows A26 Fab-Fv inhibits a human mixed lymphocyte reaction (MLR)

Figure 12B:
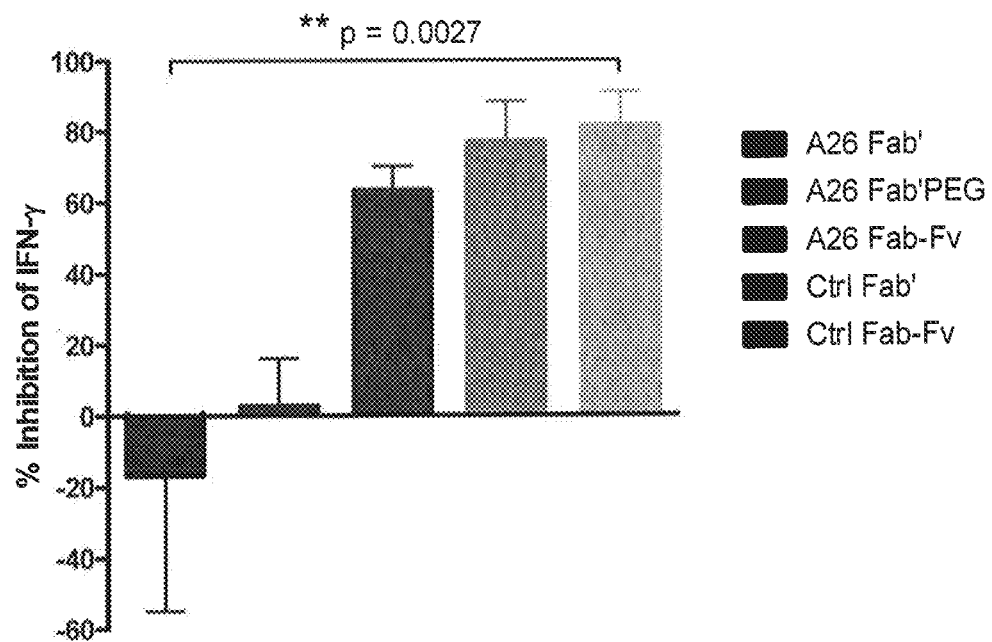
FIG. 12B shows A26 Fab-Fv inhibits IFN-gamma production during a human MLR

FIG. 12B shows A26 Fab-Fv inhibits IFN-gamma production during a human MLR

Figure 13:
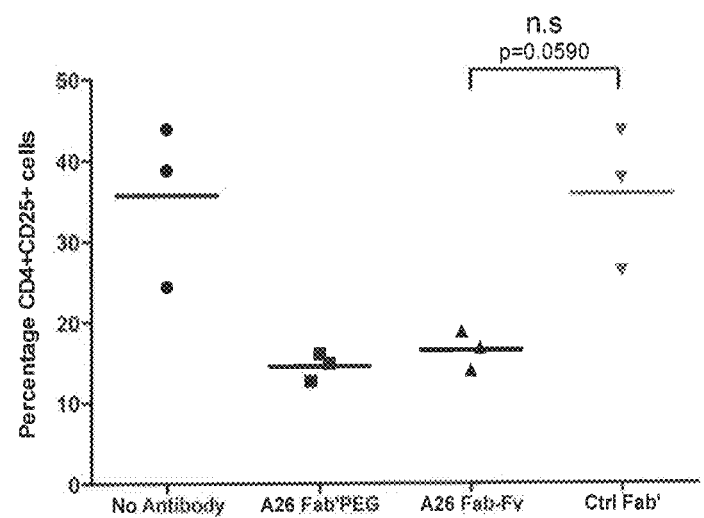
FIG. 13 shows A26 Fab-Fv reduces the percentage of activated (CD25+) CD4+ T cells after secondary antigen re-stimulation with *Dermatophagoides pteronyssinus* allergenic extract
Figure 14A:
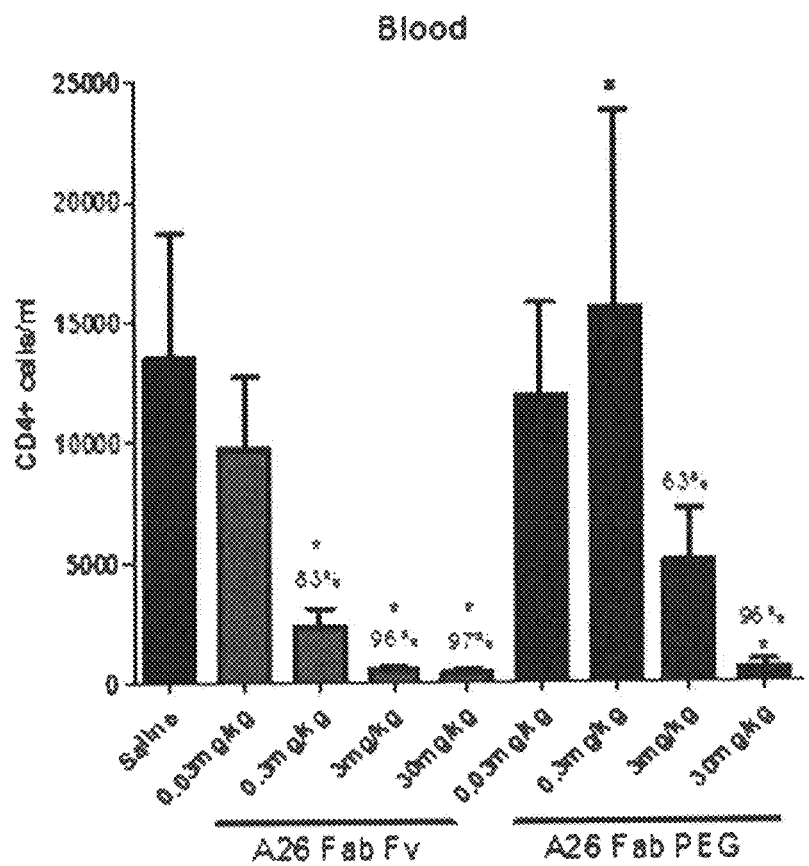
FIG. 14A shows A26 Fab-Fv administered prior to cell transfer dose dependently inhibits CD4$^+$ T cell proliferation in the blood in the Hu-NSG model.

FIG. 13 shows A26 Fab-Fv reduces the percentage of activated (CD25+) CD4+ T cells after secondary antigen re-stimulation with *Dermatophagoides pteronyssinus* allergenic extract FIG. 14A shows A26 Fab-Fv administered prior to cell transfer dose dependently inhibits CD4+ T cell proliferation in the blood in the Hu-NSG model.

Figure 14B:
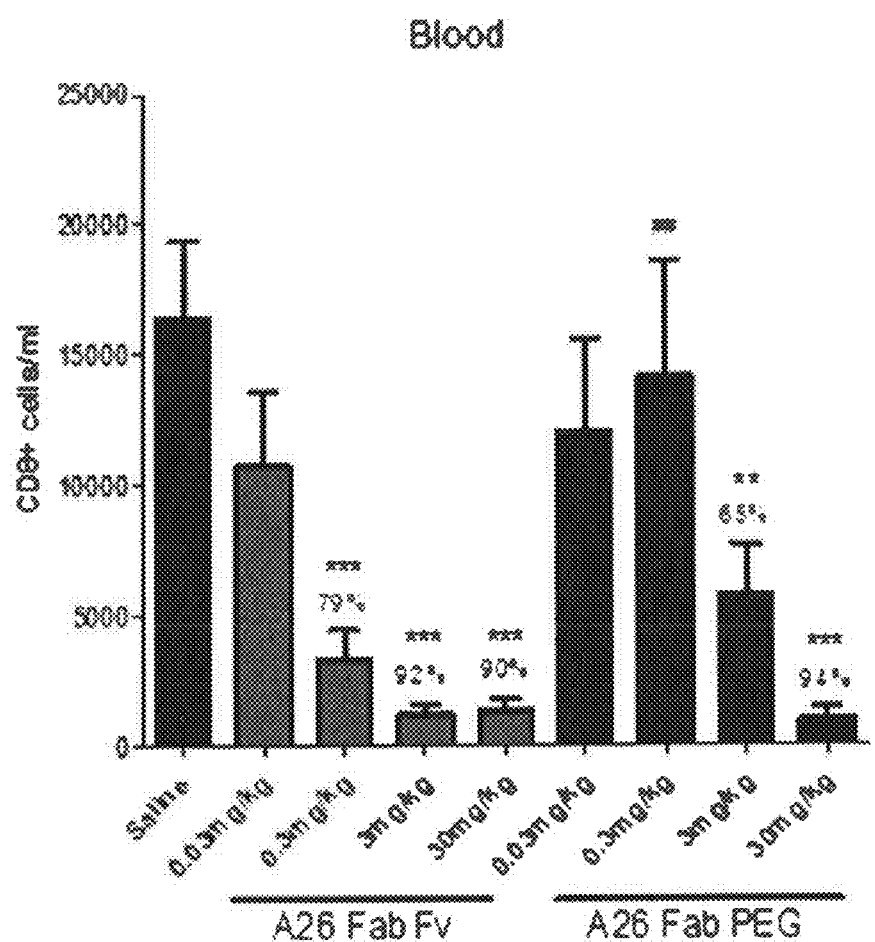
FIG. 14B shows A26 Fab-Fv administered prior to cell transfer dose dependently inhibits CD8$^+$ T cell proliferation in the blood in the Hu-NSG model.

FIG. 14B shows A26 Fab-Fv administered prior to cell transfer dose dependently inhibits CD8$^+$ T cell proliferation in the blood in the Hu-NSG model.

Figure 14C:
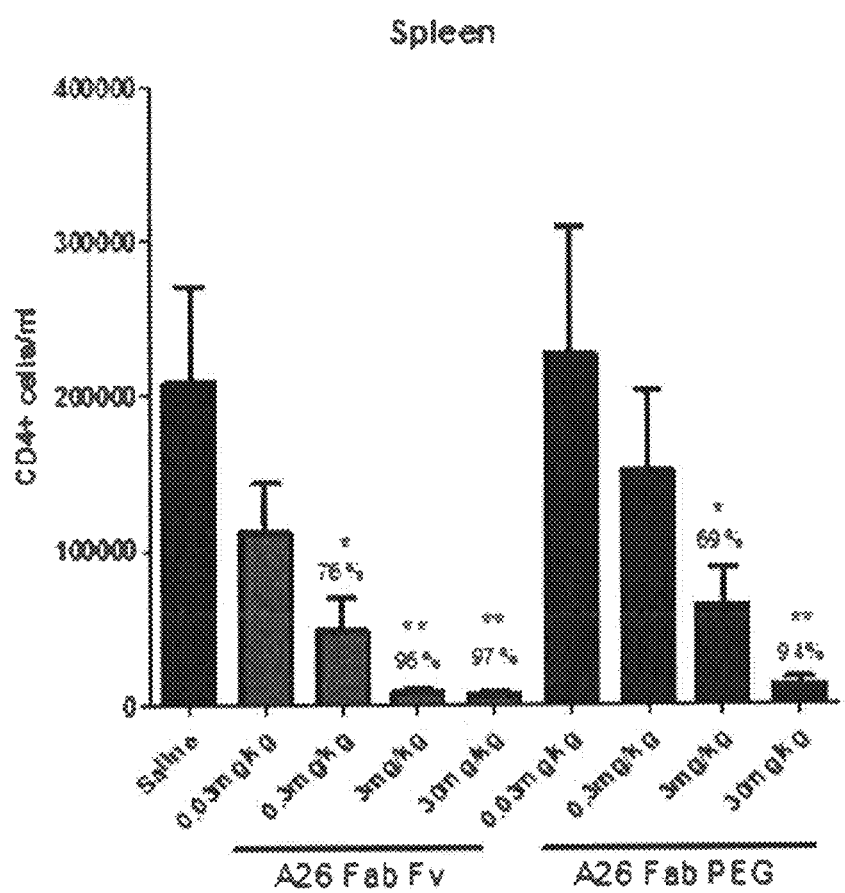
FIG. 14C shows A26 Fab-Fv administered prior to cell transfer dose dependently inhibits CD4$^+$ T cell proliferation in the spleen in the Hu-NSG model.

FIG. 14C shows A26 Fab-Fv administered prior to cell transfer dose dependently inhibits CD4$^+$ T cell proliferation in the spleen in the Hu-NSG model.

Figure 14D:
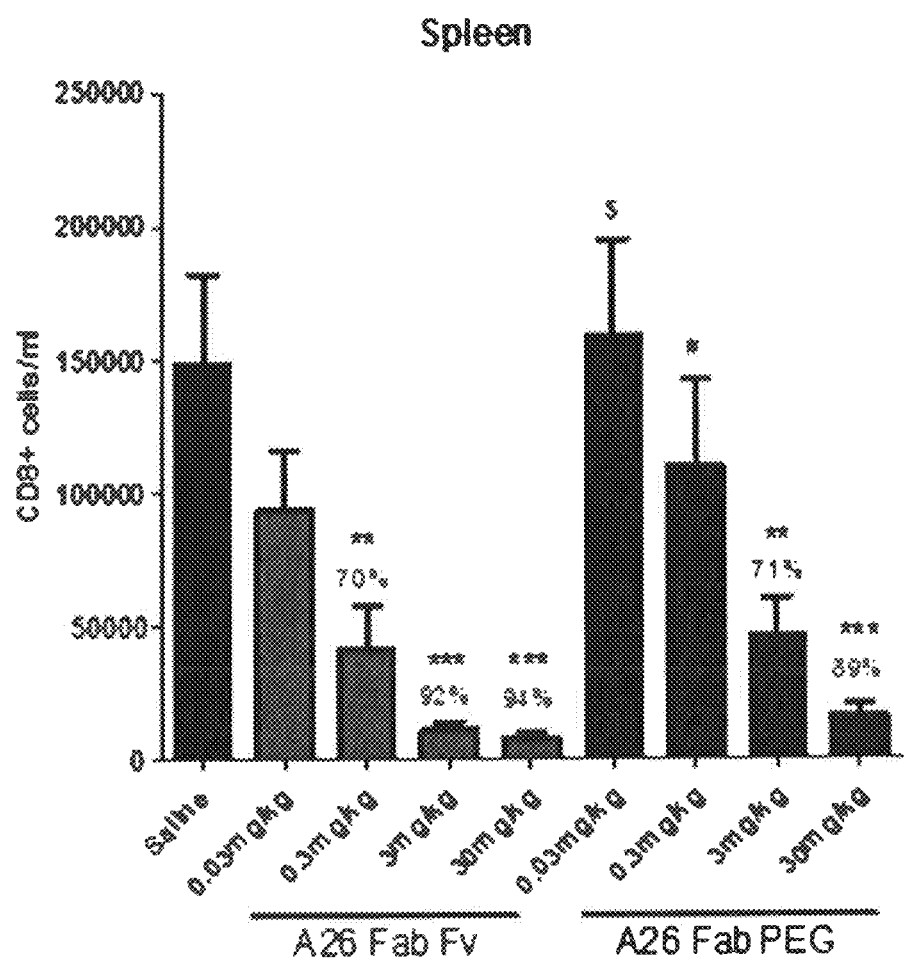
FIG. 14D shows A26 Fab-Fv administered prior to cell transfer dose dependently inhibits CD8$^+$ T cell proliferation in the spleen in the Hu-NSG model.

FIG. 14D shows A26 Fab-Fv administered prior to cell transfer dose dependently inhibits CD8$^+$ T cell proliferation in the spleen in the Hu-NSG model.

DNA Manipulations and General Methods

Competent *E. coli* strains were used for transformations and routine culture growth. DNA restriction and modification enzymes were obtained from Roche Diagnostics Ltd. and New England Biolabs. Plasmid preparations were performed using Maxi Plasmid purification kits (QIAGEN, catalogue No. 12165). DNA sequencing reactions were performed using the ABI Prism Big Dye terminator sequencing kit (catalogue No. 4304149) and run on an ABI 3100 automated sequencer (Applied Biosystems). Data was analysed using the program Sequencher (Genecodes). Oligonucleotides were obtained from Simga or Invitrogen. Genes encoding initial V-region sequences were constructed by an automated synthesis approach by DNA2.0, and modified to generate the grafted versions by oligonucleotide directed mutagenesis. The concentration of Fab-Fv was determined by a Protein-G based HPLC method.

Example 1

Generation and Analysis of Different Humanisation Grafts of 645 in A26Fab-645dsFv We have previously described the Fab-dsFv antibody format (FIG. 1) (sometimes referred to herein simply as Fab-Fv) and a humanised anti-albumin antibody known as '645gH1gL1' in WO2010/035012. We have also previously described the generation of a humanised antagonistic anti-OX40 antibody known as 'A26' and a PEGylated Fab' fragment thereof in WO2010/096418. Here we describe the generation of a new improved humanised graft of antibody '645' known as 645dsgH5gL4 and the generation of a Fab-dsFv antibody molecule incorporating that graft in the Fv component and the 'A26' variable regions in the Fab component. The variable regions of A26 are given in FIGS. 2A and 2B (SEQ ID NOs 7 and 8).

The variable and constant region sequences of A26 combined are given in FIGS. 2D and 2E (SEQ ID NOs 9 and 10).

The sequences of 645gH1 and gL1 are given in FIGS. 4A and 4B, SEQ ID NOs 17 and 18. Where the term Fab'-PEG or A26 Fab'-PEG is used this refers to the A26 Fab-40K PEG' described in WO2010/096418.

1.1. Construction of A26Fab-645dsFv(gH1gL1) and A26Fab-645dsFv(gH5gL4)G4S Linker Plasmids The total coding region of A26Fab-645dsFv(gL1) light chain (SEQ ID NO:20) was cloned into a UCB mammalian expression vector under the control of the HCMV-MIE promoter and SV40E polyA sequence. The light chain variable region of 645dsFv(gL1) (SEQ ID NO:18) was mutated to 645dsFv(gL4) (SEQ ID NO:12) by an overlapping PCR method. The total coding region of A26Fab-645dsFv(gH1) heavy chain (SEQ ID NO:19 was cloned into a UCB mammalian expression vector under the control of the HCMV-MIE promoter and SV40E polyA sequence. The heavy chain variable region of 645dsFv(gH1) (SEQ ID NO:17) was mutated to 645dsFv(gH5) (SEQ ID NO:11) by an overlapping PCR method. The constructs were verified by sequencing. Both constructs contained the 3×G4S linker given in SEQ ID NO:14, FIG. 3D.

1.2 Mammalian Expression of A26Fab-645dsFv(gH1gL1) and A26Fab-645dsFv(gH5gL4)

HEK293 cells were transfected with the heavy and light chain plasmids using Invitrogen's 293fectin transfection reagent according to the manufacturer's instructions. Briefly, 25 μg heavy chain plasmid and 25 μg light chain plasmid were incubated with 100 μl 293fectin and 1700 μl Optipro media for 20 mins at RT. The mixture was then added to 50×10⁶ HEK293 cells in 50 ml suspension and incubated for 6 days with shaking at 37° C. After 6 days the supernatant was collected by centrifugation at 1500×g for 10 minutes to remove the cells and then 0.22 μm sterile filtered.
1.3 Protein-G Purification of A26Fab-645dsFv(gH1gL1) and A26Fab-645dsFv(gH5gL4)

The ~50 ml of 0.22 μm filtered supernatants were concentrated to ~2 ml using Amicon Ultra-15 concentrators with a 10 kDa molecular weight cut off membrane and centrifugation at 4000×g in a swing out rotor. 1.8 ml of concentrated supernatant was applied at 1 ml/min to a 1 ml Gammabind Plus Sepharose (GE Healthcare) column equilibrated in 20 mM phosphate, 40 mM NaCl pH7.4. The column was washed with 20 mM phosphate, 40 mM NaCl pH7.4 and the bound material eluted with 0.1M glycine/HCl pH2.7. The elution peak was collected and pH adjusted to ~pH7 with 2M Tris/HCl pH8.5. The pH adjusted elution was concentrated and diafiltered into 20 mM phosphate, 150 mM NaCl pH7.4 using Amicon Ultra-15 concentrators with a 10 kDa molecular weight cut off membrane and centrifugation at 4000×g in a swing out rotor, to a final volume of ~0.3 ml.
1.4 Size Exclusion Analysis A26Fab-645dsFv(gH1gL1) and A26Fab-645dsFv(gH5gL4)

Protein-G purified samples were analysed by size exclusion HPLC. The samples were separated on a Superdex 200 10/300 GL Tricorn column (GE Healthcare) developed with an isocratic gradient of PBS pH7.4 at 1 ml/min. Peak detection was at 280 nm and apparent molecular weight was calculated by comparison to a standard curve of known molecular weight proteins verses elution volume. Changing the humanisation graft of the 645dsFv from gH1gL1 to gH5gL4 resulted in an increase in the percentage monomer of the expressed A26Fab-645dsFv from 59% to 71% an increase of 12%, without any change in the thermal stability of the dsFv (data not shown) or in the affinity of binding of the dsFv to HSA (data not shown).

Example 2

2.1 BIAcore Kinetics for A26 Fab-dsFv (645gH5gL4) Binding OX40

In this and all subsequent examples the A26 Fab-dsFv 645gH5gL4 had the heavy chain sequence given in SEQ ID NO:15 (FIG. 3E) and the light chain sequence given in SEQ ID NO:16 (FIG. 3F) i.e. the heavy chain contained the G4S, G4T, G4S linker given in SEQ ID NO:13, FIG. 3C.

BIA (Biamolecular Interaction Analysis) was performed using a BIAcore T200 (GE Healthcare). Affinipure F(ab')₂ Fragment goat anti-human IgG, F(ab')₂ fragment specific (Jackson ImmunoResearch) was immobilised on a CM5 Sensor Chip via amine coupling chemistry to a capture level of ≈5000 response units (RUs). HBS-EP buffer (10 mM HEPES pH 7.4, 0.15 M NaCl, 3 mM EDTA, 0.05% Surfactant P20, GE Healthcare) was used as the running buffer with a flow rate of 10 μL/min. A 10 μL injection of A26 Fab' at 0.5 μg/mL or A26Fab-dsFv at 1 μg/mL was used for capture by the immobilised anti-human IgG-F(ab')₂. Human OX40 was titrated over the captured A26 at various concentrations (25 nM to 1.5625 nM) at a flow rate of 30 μL/min. The surface was regenerated by 2×10 μL injection of 50 mM HCl, followed by a 5 μL injection of 5 mM NaOH at a flowrate of 10 μL/min. Background subtraction binding curves were analysed using the T200evaluation software (version 1.0) following standard procedures. Kinetic parameters were determined from the fitting algorithm.

TABLE 1

| Average of 4 determinations | | | | |
|---|---|---|---|---|
| Sample | ka(1/Ms) | kd(1/s) | KD(M) | KD(pM) |
| Fab' | 2.18 ± 0.38E+05 | 1.00E−05 | 4.68E−11 | 46.8 |
| Fab-Fv | 2.55 ± 0.35E+05 | 1.04E−05 | 4.12E−11 | 41.2 |
| Fab' PEG | 2.33 ± 0.46E+05 | 1.12E−05 | 4.84E−11 | 48.4 |

2.2. BIAcore Kinetics for A26 Fab-dsFv (645gH5gL4) Binding Albumin

BIA (Biamolecular Interaction Analysis) was performed using a BIAcore T200 (GE Healthcare). Affinipure F(ab')₂ Fragment goat anti-human IgG, F(ab')₂ fragment specific (Jackson ImmunoResearch) was immobilised on a CM5 Sensor Chip via amine coupling chemistry to a capture level of ≈5000 response units (RUs). HBS-EP buffer (10 mM HEPES pH 7.4, 0.15 M NaCl, 3 mM EDTA, 0.05% Surfactant P20, GE Healthcare) was used as the running buffer with a flow rate of 10 μL/min. A 10 μL injection of Fab-Fv at 0.75 μg/mL was used for capture by the immobilised anti-human IgG-F(ab')₂. Human Serum Albumin (HSA), Mouse Serum albumin (MSA) and Cynomolgus Serum Albumin (CSA) was titrated over the captured Fab-Fv at various concentrations (50 nM to 6.25 nM) at a flow rate of 30 μL/min. The surface was regenerated by 2×10 μL injection of 50 mM HCl, followed by a 5 μL injection of 5 mM NaOH at a flowrate of 10 μL/min. Background subtraction binding curves were analysed using the T200evaluation software (version 1.0) following standard procedures. Kinetic parameters were determined from the fitting algorithm.

TABLE 2

| Average of 3 determinations | | | | |
|---|---|---|---|---|
| Sample | ka(1/Ms) | kd(1/s) | KD(M) | KD(nM) |
| HAS | 5.84E+04 | 1.63E−04 | 2.93E−09 | 2.93 |
| MSA | 8.86E+04 | 3.68E−04 | 4.16E−09 | 4.16 |
| CSA | 7.1E+04 | 1.89E−04 | 2.66E−09 | 2.66 |

2.3 Demonstration of A26 Fab-dsFv(645gH5gL4) Binding OX40 and Albumin Simultaneously The simultaneous binding of human OX40 and Human Serum Albumin to A26 Fab-dsFv was assessed. The A26 Fab-dsFv construct was captured to the sensor chip surface as stated in the method for Biacore kinetics for binding A26 Fab-dsFv albumin. 50 nM HAS, 25 nM OX40 or a mixed solution with final concentration of 50 nM HSA and 25 nM OX40 were titrated separately over the captured A26 Fab-dsFv. The binding response for the combined HSA/OX40 solution was equivalent to the sum of the responses of the independent injections. This confirms that the Fab-dsFv is capable of simultaneous binding to both human OX40 and HSA.

TABLE 3

| Sample | Analyte | Binding (RU) |
|---|---|---|
| A26 Fab-Fv | hOX40 | 25 |
| | HSA | 9 |
| | hOX40 + HSA | 35 (34) |

2.4 Cell-Based Affinity of A26 Fab-dsFv (645gH5gL4)

Methods:

A26 Fab-Fv Binding to Human Activated CD4+ OX40+ T Cells.

PBMC were isolated by separation on a Ficoll gradient and activated with 4 µg/mL PHA-L for 3 days at 37° C., 5% $CO_2$, 100% humidity. CD4+ T cells were isolated by negative selection using magnetic beads (CD4+ T cell Isolation Kit II for Human; Miltenyi Biotec). Approximately $1 \times 10^5$ cells were incubated in the presence of antibody in either Facs buffer (PBS/0.2% BSA/0.09% NaN3) or Facs buffer supplemented with 5% HSA at 4° C. The final concentration of the antibody ranged from 48 nM-0.0005 nM)). The cells were washed in PBS prior to analysis by flow cytometry using a FACScalibur (Becton Dickinson). Two titration data sets were produced in both buffer conditions, one with A26 Fab-dsFv and the second with an irrelevant control Fab-Fv to determine non-specific binding. The number of moles of bound antibody were calculated by using interpolated values from a standard curve generated by use of beads comprised of differing but known amounts of fluorescent dye. Geometric mean fluorescence values were determined in the flow cytometric analyses of cells and beads. Non-specific binding was subtracted from the A26 Fab-dsFv values and the specific binding curve thus generated analysed by non-linear regression using a one-site binding equation (Graphpad Prism®) to determine the $K_D$.

To determine the affinity of A26 Fab-dsFv for cell surface expressed antigen, saturation binding experiments were performed using activated CD4+ OX40+ T cells, and Alexa Fluor 488-labelled A26 Fab-dsFv. Specific binding of antibody to receptor at equilibrium across a range of antibody concentrations was used to determine $K_D$, assuming that only a very small fraction of antibody was bound to receptor at any point on the binding curve.

Equilibrium binding is described using the following equation:

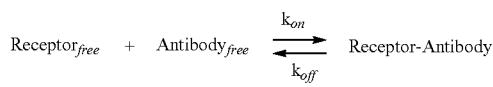

The rate of association of antibody with receptor=$k_{on} \times [\text{Receptor}_{free}] \times [\text{Antibody}_{free}]$ The rate of dissociation of receptor-antibody complex=$k_{off} \times [\text{Receptor-Antibody}]$ At equilibrium, the association and dissociation rates are equal and an equation can be derived which describes the binding isotherm; on a semi-log plot the binding is sigmoidal. The $K_D$ is defined by $k_{off}/k_{on}$ and can be calculated from the binding curve as the concentration at which half-maximal binding occurs.

Binding of AlexaFluor488-labelled A26 Fab-Fv to activated human CD4+OX40+ T cells was measured by flow cytometry across a 5-log concentration range.

A representative binding curve for A26 Fab-Fv is shown in FIG. 9A.

The mean $K_D$ value obtained on activated cells from 5 different donors is 145 pM.

A comparator binding curve for A26 Fab, A26 Fab-Fv and A26 Fab-PEG is shown in FIG. 9B The graphs represents the mean of 4 or 5 experiments where a different donor was used in each experiment.

PBMC were isolated by separation on a Ficoll gradient and activated with 4 µg/mL PHA-L for 3 days at 37° C., 5% $CO_2$, 100% humidity. Following this, CD4+ T cells were isolated by negative selection using magnetic beads (CD4+ T cell Isolation Kit II for Human; Miltenyi Biotec). Approximately $1 \times 10^5$ cells were incubated in the presence of antibody in either Facs buffer (PBS/0.2% BSA/0.09% NaN3) or Facs buffer supplemented with 5% HSA, at 4° C. The final concentration of the antibody ranged from 48 nM-0.0005 nM. The cells were washed in PBS prior to analysis by flow cytometry using a FACScalibur (Becton Dickinson). Titration data sets were also produced for isotype control antibodies for each A26 format to determine non specific binding. The number of moles of bound antibody was calculated by using interpolated values from a standard curve generated from beads comprised of differing but known amounts of fluorescent dye. Geometric mean fluorescence values were determined in the flow cytometric analyses of cells and beads. Non-specific binding was subtracted from the A26 Fab-Fv values and the specific binding curve thus generated analysed by non-linear regression using a one-site binding equation (Graphpad Prism®) to determine the $K_D$.

TABLE 4

Mean $K_D$ values for A26 antibodies in human cell affinity assays

| Antibody Format | Cellular Affinity HSA $K_D$ (nM) ± S.E.M | Cellular Affinity NO HSA $K_D$ (nM) ± S.E.M |
| --- | --- | --- |
| A26 Fab-Fv (n = 5) | 0.145 ± 0.019 | 0.096 ± 0.017 |
| A26 Fab'PEG (n = 4) | 0.230 ± 0.057 | 0.322 ± 0.089 |
| A26 Fab' (n = 4) | 0.068 ± 0.011 | 0.085 ± 0.031 |

Example 3

A26 Fab-Fv Modulates Cytokine Production from PBMC Exposed to *Dermatophagoides pteronyssinus* Allergenic Extract PBMC were isolated from allergic volunteers by separation on a Ficoll gradient. Purified PBMC were exposed to 25 µg/mL *Dermatophagoides pteronyssinus* allergenic extract in the presence of test antibody (concentration range 50 µg/mL to 0.0005 µg/mL) in a final volume of 200 µL per well in a 96-well round-bottomed plate. After 6 days incubation at 37° C., 5% $CO_2$, 100% humidity, supernatants were harvested and assayed for IL-13 content by MSD. The graph in FIG. 10A shows representative data of 1 representative donor from 4, where the mean EC50 for inhibition of IL-13 production was 0.87 nM (range from 0.6 nM to 1.07 nM).

TABLE 5

Mean $EC_{50}$ values for A26 Antibodies in human HDM in vitro assays

| Antibody Format | Inhibition of IL-13 Production $EC_{50}$ (NM) ± S.E.M | Inhibition of IL-5 Production $EC_{50}$ (nM) ± S.E.M |
| --- | --- | --- |
| A26 Fab-Fv (n = 4) | 0.865 ± 0.112 | 0.785 ± 0.216 |
| A26 Fab'PEG (n = 4) | 0.928 ± 0.282 | 1.310 ± 0.425 |
| A26 Fab' (n = 4) | 0.335 ± 0.040 | 0.680 ± 0.223 |

$EC_{50}$ values were calculated from individual donor inhibition curves by non-linear regression using Graphpad Prism ® software A26 Fab-Fv Reduces the Percentage of Activated (CD25+) CD4+ T Cells after Secondary Antigen Re-Stimulation with

*Dermatophagoides pteronyssinus* Allergenic Extract CD4+ T cells from allergic donors were stimulated in vitro for 7 days with 25 µg/ml *Dermatophagoides pteronyssinus* allergenic extract (Greer) and autologous APC, in the presence of no antibody or 10 ng/ml A26 Fab'PEG, A26 Fab-Fv or Ctrl Fab' (A33 Fab'). Cells were washed and rested for 3 days and then re-stimulated with *Dermatophagoides pteronyssinus* extract as previously (FIG. 13). After 3 days, the cells were washed and fluorescently stained for surface CD3, CD4 and CD25. Cells were then analysed by flow cytometry on a FACS Canto flow cytometer (BD). Cells were gated on live lymphocytes and CD3+CD4+ expression prior to analysis. Data represents n=3 donors including mean. n.s, A26 Fab-Fv compared to Ctrl Fab' (significance measured using paired, 2 tailed T test).

Example 4

A26 Fab-Fv Inhibits CD4+ and CD8+ T Cell Proliferation in a Hu-NSG Mouse Model

Mice were dosed s.c with 0.03, 0.3, 3 or 30 mg/kg A26 Fab-Fv one day prior to transfer of $1 \times 10^7$ human PBMCs into the peritoneal cavity. After 14 days mice were bled by cardiac puncture under terminal aesthetic and then killed by cervical dislocation. The number of human CD4+ and CD8+ cells in the blood was then determined by FACS analysis (FIG. 10B). Data (n=10) is expressed as means±SEM and statistical analysis is by one way ANOVA with Bonferroni post test. Values represent % inhibition±SEM.

Results are shown in FIGS. 14A-B.

The Hu-NSG model has demonstrated that A26 Fab-Fv profoundly inhibits human T cell proliferation in vivo and supports A26 Fab-Fv as a viable therapeutic candidate for the inhibition of T cell mediated pathologies. In addition, the Fab-Fv format conferred greater efficacy at lower doses than the Fab' PEG format. The decrease in this xeno-proliferative response of donor T cells may provide supporting evidence that A26 Fab-Fv could be a viable therapeutic for GVHD.

Example 5

Ligand-Blocking Capacity

The capacity of A26 Fab-dsFv to block the interaction between cell-surface expressed OX40 and recombinant OX40L was measured using a flow cytometry-based ligand blocking assay. Briefly, activated human CD4+OX40+ T cells were pre-incubated with a titration of A26 Fab-Fv. Recombinant OX40L was subsequently added to the cells and allowed to bind in the presence of A26 Fab-dsFv. The proportion of OX40L bound was then detected by flow cytometry using a labelled secondary reagent. FIG. 11 shows an inhibition curve representing combined data from 3 independent donors and demonstrates that A26 Fab-dsFv is capable of completely blocking OX40L binding. The mean $IC_{50}$ for inhibition of recombinant OX40L binding was 0.44 nM (n=3 donors).

Methods: Inhibition of OX40L Binding to Human Activated CD4+OX40+ T Cells by A26 Fab-Fv PBMC were isolated by separation on a Ficoll gradient and activated with 4 µg/mL PHA-L (Sigma) for 3 days at 37° C., 5% $CO_2$, 100% humidity. CD4+ T cells were then purified from the culture by negative selection using MACS columns (Miltenyi Biotech, CD4+ T cell isolation kit II). $2 \times 10^5$ CD4+ T cells were incubated in the presence of A26 Fab-dsFv (final concentration range 10 µg/mL-0.000056 µg/mL (136.6 nM-0.000765 nM)) for 30 minutes at 4° C. OX40L (biotinylated CD252 muCD8, Ancell) was added at a final concentration of 2 µg/mL and incubated for a further 30 minutes at 4° C. Cells were washed and OX40L binding detected by incubation with PE-labelled streptavadin (Jackson Immunoresearch) prior to analysis by flow cytometry using a FACS Canto (Becton Dickinson). A matched non-OX40 binding Fab-dsFv was used as a control. The inhibition curve was analysed by non-linear regression (Graphpad Prism®) to determine the $IC_{50}$. An inhibition curve representing combined data from 3 independent donors is shown in FIG. 11, where data points represent the mean and error bars represent SEM.

The mean $EC_{50}$ for inhibition of recombinant OX40L binding to OX40 by A26 Fab-Fv was 0.445 nM. In comparison, A26 Fab'PEG was slightly less potent at ligand blocking ($EC_{50}$=0.739 nM) whereas A26 Fab' had marginally greater potency ($EC_{50}$=0.242 nM) than the Fab-Fv as shown below.

TABLE 6

$EC_{50}$ values for inhibition of OX40L binding to human activated CD4+OX40+ T cells by A26 antibodies

| Antibody format | $EC_{50}$ ligand blocking (nM) Mean ± S.E.M. |
|---|---|
| A26 Fab-Fv (n = 3) | 0.445 ± 0.110 |
| A26 Fab'PEG (n = 3) | 0.739 ± 0.166 |
| A26 Fab' (n = 3) | 0.242 ± 0.069 |

$EC_{50}$ values were calculated from individual donor inhibition curves by non-linear regression using Graphpad Prism® software.

Example 6

Effect of A26 Fab-Fv in Functional Human In Vitro Assays

The effect of A26 Fab-Fv on OX40-OX40L dependent cellular interactions was assessed in a range of antigen-driven human lymphocyte assays. These assays were performed in the presence of 5% human serum to ensure saturation of the albumin binding site of the Fv region, as would be predicted to occur in vivo.

A26 Fab-Fv Inhibits a Mixed Lymphocyte Reaction

The one-way allogeneic mixed lymphocyte reaction (MLR) is an in vitro model of alloreactive T cell activation and proliferation (Bach et al., 1964, O'Flaherty et al., 2000). Donor T cells are activated through recognition of allogeneic MHC antigens on unrelated donor stimulator PBMCs, resulting in cellular proliferation and cytokine production (Lukacs et al., 1993). T lymphocyte alloreaction has been shown to be driven by both the allogeneic MHC antigen and bound peptide (Sherman et al., 1993). The magnitude of an MLR response correlates with the degree of MHC mismatching between the responder-stimulator pair (Forrester et al., 2004). An MLR response results in the proliferation of cells from the responding donor and the production of both Th1 (IL-2, IFN-γ and TNF-α) and Th2 (IL-4, IL-5, IL-10 and IL-13) T cell derived cytokines. The exact cytokine profile in an MLR is thought to be specific to the responder-stimulator pairing (Jordan et al., 2002). MLR assays have been used widely in research to study T cell activation pathways, screen immunosuppressive drugs and predict possible donor organ rejection in transplant recipients (Bromelow et al., 2001).

The effect of A26 Fab-Fv on in vitro human alloreactive T cell activation and proliferation was investigated using an MLR assay essentially as described by O'Flaherty et al., 2000. PBMCs from two unrelated donors were co-cultured in the presence or absence of A26 Fab-Fv, A26 Fab' or A26

Fab'PEG and cellular proliferation measured by $^3$H-thymidine incorporation. As shown in FIG. 12A, A26 Fab-Fv inhibited cellular proliferation in a concentration-dependent manner with an $EC_{50}$ value of 0.56 nM (40.9 ng/mL) and a maximal inhibition of 55% (n=3 donor pairings). A26 Fab-Fv was slightly more potent than A26 Fab'PEG, which had an $EC_{50}$ value of 0.88 nM, while A26 Fab' had an $EC_{50}$ value of 0.25 nM as shown in Table 7.

Human PBMCs from two unrelated donors were isolated from whole blood. Cells from one donor were inactivated by γ-irradiation to generate the stimulator population. Cells from the remaining donor formed the responder population. Stimulator and responder populations were mixed at a 1:1 ratio (1×10$^5$ cells/donor) and cultured in the presence A26 Fab', A26 Fab-Fv or A26 Fab'PEG (0.4 ng-25 µg/mL) for 6 days. In-house reagent CA162-01297.1 Fab-Fv was utilized as an isotype-matched control. Cellular proliferation was measured at day 6 by $^3$H-thymidine incorporation (0.5 µCi/well). Data is displayed as percentage inhibition relative to the responder plus stimulator response in the absence of biologic reagent, and is the combined data from three donor pairings. $EC_{50}$ values were calculated using Graphpad Prism® software.

TABLE 7

$EC_{50}$ values for inhibition of human MLR proliferative response by A26 antibodies

| Antibody format | $EC_{50}$ (nM) Mean ± S.E.M. |
| --- | --- |
| A26 Fab-Fv (n = 3) | 0.56 ± 0.12 |
| A26 Fab'PEG (n = 3) | 0.88 ± 0.44 |
| A26 Fab' (n = 3) | 0.25 ± 0.06 |

Supernatants from the human MLR were also analysed to investigate the effect of A26 Fab-Fv on cytokine production. As shown in FIG. 12B, A26 Fab-Fv significantly inhibited production of IFN-γ in the MLR by an average of 81% (n=3 donor pairings). Human PBMCs from two unrelated donors were isolated from whole blood. Cells from one donor were inactivated by γ-irradiation to generate the stimulator population. Cells from the remaining donor formed the responder population. Stimulator and responder populations were mixed at a 1:1 ratio (1×10$^5$ cells/donor) and cultured in the presence of 25 µg/ml A26 Fab', A26 Fab-Fv or A26 Fab'PEG or controls (A33 Fab' or CA162.01297.1) for 6 days. Supernatants were harvested and assayed for IFN-γ content using an MSD assay. The percent inhibition was calculated relative to cells cultured with no antibody. The graphs represent pooled data from three donors (mean±S.E.M). **=p<0.01; A26 Fab-Fv compared with Ctrl Fab-Fv (significance measured using paired, 2-tailed T-test).

Example 7

A26 Fab-Fv Binding to NK Cells in a Human MLR

The effect of A26 Fab-Fv on NK cell division within an MLR was investigated. T lymphocyte alloreaction drives the mixed lymphocyte response and A26 Fab-Fv profoundly inhibits T cell division and IFNγ production in this system. Inhibition of NK cell division could also contribute to reduced IFNγ production. Using CFSE-labelled responder cells inhibition of NK cell division was demonstrated by FACS analysis of the dividing population (data not shown). Two different measures of cell division are shown. The Division Index represents the average number of cell divisions that a cell in the original population has undergone and includes the undivided cells; A26 Fab-Fv reduces the Division Index indicating that fewer cells in the population are committed to division; this effect is presumably mediated by the NK cells that are expressing OX40. The Proliferation Index reflects proliferation of the responding population only, and the inhibitory effect of A26 Fab-Fv using this measure is relatively reduced.

Example 8

Mean $K_D/EC_{50}$ Values for A26 Fab-Fv in Human In Vitro Assays

| Binding/Functional Assay | Mean $K_D/EC_{50}$ (nM) ± S.E.M. | Mean $K_D/EC_{50}$ (µg/mL) |
| --- | --- | --- |
| Affinity (n = 5) | 0.145 ± 0.019 | 0.011 |
| OX40L blocking (n = 3) | 0.445 ± 0.110 | 0.033 |
| Mixed Lymphocyte Reaction - Inhibition of Proliferation (n = 3) | 0.558 ± 0.121 | 0.041 |
| House Dust Mite - Inhibition of IL-13 production (n = 4) | 0.865 ± 0.112 | 0.063 |

It will of course be understood that the present invention has been described by way of example only, is in no way meant to be limiting, and that modifications of detail can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication were specifically and individually indicated to be incorporated by reference herein as though fully set forth.

What is claimed is:

1. A method for the treatment of a pathological disorder in a subject in need thereof, the method comprising administering to the subject a bispecific antibody fusion protein that comprises:
   a heavy chain comprising, in sequence from the N-terminal, a first heavy chain variable domain ($V_H1$), a CH1 domain and a second heavy chain variable domain ($V_H2$), and
   a light chain comprising, in sequence from the N-terminal, a first light chain variable domain ($V_L1$), a CL domain and a second light chain variable domain ($V_L2$),
   wherein said heavy and light chains are aligned such that $V_H1$ and $V_L1$ form a first antigen binding site and $V_H2$ and $V_L2$ form a second antigen binding site,
   wherein the antigen bound by the first antigen binding site is human OX40 and the antigen bound by the second antigen binding site is human serum albumin,
   wherein the first variable domain of the heavy chain ($V_H1$) comprises the sequence given in SEQ ID NO:1 for CDR-H1, the sequence given in SEQ ID NO:2 for CDR-H2 and the sequence given in SEQ ID NO:3 for CDR-H3 and the first variable domain of the light chain ($V_L1$) comprises the sequence given in SEQ ID NO:4 for CDR-L1, the sequence given in SEQ ID NO:5 for CDR-L2 and the sequence given in SEQ ID NO:6 for CDR-L3,
   wherein the second heavy chain variable domain ($V_H2$) has the sequence given in SEQ ID NO:11 and the second light chain variable domain ($V_L2$) has the sequence given in SEQ ID NO: 12; and
   the second heavy chain variable domain ($V_H2$) and second light chain variable domain ($V_L2$) are linked by a disulphide bond; and
   wherein the pathological disorder is allergy, an autoimmune disease, chronic obstructive pulmonary disease, rheumatoid arthritis, asthma, Crohn's disease, graft versus host disease, Graves' disease, Henoch-Schönlein purpura, an inflammatory disease, lupus nephritis, multiple sclerosis, myasthenia gravis, type-1 diabetes, ulcerative colitis, systemic lupus erythematosus, systemic sclerosis, transplant rejection, viral-induced lung inflammation, Wegener's granulomatosis, inflammatory bowel disease, pelvic inflammatory disease, Peyronie's disease, coeliac disease, peritonitis, psoriasis, vasculitis, meningoencephalitis, autoimmune uveitis, an immune-mediated inflammatory disorder of the central and peripheral nervous system, multiple sclerosis, Guillain-Barré syndrome, atopic dermatitis, autoimmune hepatitis, fibrosing alveolitis, IgA nephropathy, idiopathic thrombocytopenic purpura, pemphigus, primary biliary cirrhosis, sarcoidosis, scleroderma, pancreatitis, or periodontitis.

2. The method of claim 1, wherein the method comprises administering to the subject a pharmaceutical composition comprising the bispecific antibody fusion protein in combination with a pharmaceutically acceptable excipient, diluent or carrier.

3. The method of claim 2, wherein the pharmaceutical composition further comprises other active ingredients.

4. The method of claim 1, wherein the pathological disorder is an inflammatory disease.

5. The method of claim 1, wherein the pathological disorder is rheumatoid arthritis, chronic obstructive pulmonary disease, inflammatory bowel disease, Crohn's disease, ulcerative colitis, coeliac disease, psoriasis, type-1 diabetes, systemic lupus erythematosus, Guillain-Barré syndrome, atopic dermatitis, Graves' disease, idiopathic thrombocytopenic purpura graft-versus-host disease or transplant rejection.

6. The method of claim 1, wherein the pathological disorder is rheumatoid arthritis.

7. The method of claim 1, wherein the pathological disorder is inflammatory bowel disease.

8. The method of claim 1, wherein the pathological disorder is Crohn's disease, ulcerative colitis, or coeliac disease.

9. The method of claim 1, wherein the pathological disorder is atopic dermatitis.

10. The method of claim 1, wherein the pathological disorder is psoriasis.

11. The method of claim 1, wherein the pathological disorder is systemic lupus erythematosus.

12. The method of claim 1, wherein the pathological disorder is type-1 diabetes, Guillain-Barré syndrome, Graves' disease, or idiopathic thrombocytopenic purpura.

13. The method of claim 1, wherein the pathological disorder is an autoimmune disease.

14. The method of claim 1, wherein the pathological disorder is chronic obstructive pulmonary disease.

15. The method of claim 1, wherein the pathological disorder is Crohn's disease.

16. The method of claim 1, wherein the pathological disorder is Grave's disease.

17. The method of claim 1, wherein the pathological disorder is Henoch-Schönlein purpura.

18. The method of claim 1, wherein the pathological disorder is lupus nephritis.

19. The method of claim 1, wherein the pathological disorder is multiple sclerosis.

20. The method of claim 1, wherein the pathological disorder is myasthenia gravis.

21. The method of claim 1, wherein the pathological disorder is systemic sclerosis.

22. The method of claim 1, wherein the pathological disorder is type-1 diabetes.

23. The method of claim 1, wherein the pathological disorder is ulcerative colitis.

24. The method of claim 1, wherein the pathological disorder is viral-induced lung inflammation.

25. The method of claim 1, wherein the pathological disorder is Wegener's granulomatosis.

26. The method of claim 1, wherein the bispecific antibody fusion protein has a heavy chain comprising the sequence given in SEQ ID NO:15 and a light chain comprising the sequence given in SEQ ID NO:16.

27. The method of claim 26, wherein the heavy chain consists of the sequence given in SEQ ID NO:15 and the light chain consists of the sequence given in SEQ ID NO:16.

28. The method of claim 11, wherein the bispecific antibody fusion protein has a heavy chain comprising the sequence given in SEQ ID NO:15 and a light chain comprising the sequence given in SEQ ID NO:16.

29. The method of claim 28, wherein the heavy chain consists of the sequence given in SEQ ID NO:15 and the light chain consists of the sequence given in SEQ ID NO:16.

30. A method for the treatment or prophylaxis of a pathological disorder in a subject in need thereof, the method comprising administering to the subject a bispecific antibody fusion protein that comprises:
a heavy chain comprising, in sequence from the N-terminal, a first heavy chain variable domain ($V_H1$), a CH1 domain and a second heavy chain variable domain ($V_H2$), and
a light chain comprising, in sequence from the N-terminal, a first light chain variable domain ($V_L1$), a CL domain and a second light chain variable domain ($V_L2$),
wherein said heavy and light chains are aligned such that $V_H1$ and $V_L1$ form a first antigen binding site and $V_H2$ and $V_L2$ form a second antigen binding site,
wherein the antigen bound by the first antigen binding site is human OX40 and the antigen bound by the second antigen binding site is human serum albumin,
wherein the first variable domain of the heavy chain ($V_H1$) comprises the sequence given in SEQ ID NO:1 for CDR-H1, the sequence given in SEQ ID NO:2 for CDR-H2 and the sequence given in SEQ ID NO:3 for CDR-H3 and the first variable domain of the light chain ($V_L1$) comprises the sequence given in SEQ ID NO:4 for CDR-L1, the sequence given in SEQ ID NO:5 for CDR-L2 and the sequence given in SEQ ID NO:6 for CDR-L3,
wherein the second heavy chain variable domain ($V_H2$) has the sequence given in SEQ ID NO:11 and the second light chain variable domain ($V_L2$) has the sequence given in SEQ ID NO: 12 and
the second heavy chain variable domain ($V_H2$) and second light chain variable domain ($V_L2$) are linked by a disulphide bond; and
wherein the pathological disorder is allergy, asthma, graft-versus-host disease or transplant rejection.

31. The method of claim 30, for the treatment of the pathological disorder.

32. The method of claim 30, for the prophylaxis of the pathological disorder.

33. The method of claim 30, wherein the pathological disorder is allergy.

34. The method of claim 31, wherein the pathological disorder is allergy.

35. The method of claim 32, wherein the pathological disorder is allergy.

36. The method of claim 30, wherein the pathological disorder is asthma.

37. The method of claim 31, wherein the pathological disorder is asthma.

38. The method of claim 32, wherein the pathological disorder is asthma.

39. The method of claim 30, wherein the pathological disorder is graft versus host disease.

40. The method of claim 31, wherein the pathological disorder is graft versus host disease.

41. The method of claim 32, wherein the pathological disorder is graft versus host disease.

42. The method of claim 30, wherein the pathological disorder is transplant rejection.

43. The method of claim 31, wherein the pathological disorder is transplant rejection.

44. The method of claim 32, wherein the pathological disorder is transplant rejection.

45. The method of claim 30, wherein the bispecific antibody fusion protein has a heavy chain comprising the sequence given in SEQ ID NO:15 and a light chain comprising the sequence given in SEQ ID NO:16.

46. The method of claim 45, wherein the heavy chain consists of the sequence given in SEQ ID NO:15 and the light chain consists of the sequence given in SEQ ID NO:16.

47. The method of claim 40, wherein the bispecific antibody fusion protein has a heavy chain comprising the sequence given in SEQ ID NO:15 and a light chain comprising the sequence given in SEQ ID NO:16.

48. The method of claim 47, wherein the heavy chain consists of the sequence given in SEQ ID NO:15 and the light chain consists of the sequence given in SEQ ID NO:16.

49. The method of claim 41, wherein the bispecific antibody fusion protein has a heavy chain comprising the sequence given in SEQ ID NO:15 and a light chain comprising the sequence given in SEQ ID NO:16.

50. The method of claim 49, wherein the heavy chain consists of the sequence given in SEQ ID NO:15 and the light chain consists of the sequence given in SEQ ID NO:16.

\* \* \* \* \*

UNITED STATES PATENT AND TRADEMARK OFFICE
CERTIFICATE OF CORRECTION

PATENT NO. : 9,873,735 B2
APPLICATION NO. : 14/697142
DATED : January 23, 2018
INVENTOR(S) : Ralph Adams et al.

Page 1 of 1

It is certified that error appears in the above-identified patent and that said Letters Patent is hereby corrected as shown below:

In the Claims

Column 61, Line 32, Claim 5, delete "purpura" and insert -- purpura, --.

Signed and Sealed this
Thirteenth Day of November, 2018

Andrei Iancu
*Director of the United States Patent and Trademark Office*

SEQUENCE LISTING

<160> NUMBER OF SEQ ID NOS: 28

<210> SEQ ID NO 1
<211> LENGTH: 5
<212> TYPE: PRT
<213> ORGANISM: Artificial
<220> FEATURE:
<223> OTHER INFORMATION: CDRH1

<400> SEQUENCE: 1

Asn Tyr Gly Ile His
1               5

```
<210> SEQ ID NO 2
<211> LENGTH: 17
<212> TYPE: PRT
<213> ORGANISM: Artificial
<220> FEATURE:
<223> OTHER INFORMATION: CDRH2

<400> SEQUENCE: 2

Ser Ile Ser Pro Ser Gly Gly Leu Thr Tyr Tyr Arg Asp Ser Val Lys
1               5                   10                  15
Gly

<210> SEQ ID NO 3
<211> LENGTH: 8
<212> TYPE: PRT
<213> ORGANISM: Artificial
<220> FEATURE:
<223> OTHER INFORMATION: CDRH3

<400> SEQUENCE: 3

Gly Gly Glu Gly Ile Phe Asp Tyr
1               5

<210> SEQ ID NO 4
<211> LENGTH: 11
<212> TYPE: PRT
<213> ORGANISM: Artificial
<220> FEATURE:
<223> OTHER INFORMATION: CDRL1

<400> SEQUENCE: 4

Arg Ala Thr Gln Ser Ile Tyr Asn Ala Leu Ala
1               5                   10

<210> SEQ ID NO 5
<211> LENGTH: 7
<212> TYPE: PRT
<213> ORGANISM: Artificial
<220> FEATURE:
<223> OTHER INFORMATION: CDRL2

<400> SEQUENCE: 5

Asn Ala Asn Thr Leu His Thr
1               5

<210> SEQ ID NO 6
<211> LENGTH: 9
<212> TYPE: PRT
<213> ORGANISM: Artificial
<220> FEATURE:
<223> OTHER INFORMATION: CDRL3

<400> SEQUENCE: 6

Gln Gln Tyr Tyr Asp Tyr Pro Leu Thr
1               5

<210> SEQ ID NO 7
<211> LENGTH: 108
<212> TYPE: PRT
<213> ORGANISM: Artificial
<220> FEATURE:
<223> OTHER INFORMATION: Light chain variable region of antibody A26

<400> SEQUENCE: 7

Asp Ile Gln Met Thr Gln Ser Pro Ser Ser Leu Ser Ala Ser Val Gly
1               5                   10                  15
```

```
Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
    50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg
            100                 105

<210> SEQ ID NO 8
<211> LENGTH: 117
<212> TYPE: PRT
<213> ORGANISM: Artificial
<220> FEATURE:
<223> OTHER INFORMATION: Heavy chain variable region of antibody A26

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser
        115

<210> SEQ ID NO 9
<211> LENGTH: 214
<212> TYPE: PRT
<213> ORGANISM: Artificial
<220> FEATURE:
<223> OTHER INFORMATION: Light chain of anti-OX40 antibody Fab component

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
    50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
```

```
                    85                  90                  95
Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 220
<212> TYPE: PRT
<213> ORGANISM: Artificial
<220> FEATURE:
<223> OTHER INFORMATION: Heavy chain of anti-OX40 antibody Fab component

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220
```

```
<210> SEQ ID NO 11
<211> LENGTH: 121
<212> TYPE: PRT
<213> ORGANISM: Artificial
<220> FEATURE:
<223> OTHER INFORMATION: Heavy chain of anti-albumin Fv component

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 12
<211> LENGTH: 112
<212> TYPE: PRT
<213> ORGANISM: Artificial
<220> FEATURE:
<223> OTHER INFORMATION: Light chain of anti-albumin Fv component

<400> SEQUENCE: 12

Asp Ile Gln Met Thr Gln Ser Pro Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Tyr Ser Ser Ser Ile
                85                  90                  95

Ser Asp Thr Thr Phe Gly Cys Gly Thr Lys Val Glu Ile Lys Arg Thr
            100                 105                 110

<210> SEQ ID NO 13
<211> LENGTH: 16
<212> TYPE: PRT
<213> ORGANISM: Artificial
<220> FEATURE:
<223> OTHER INFORMATION: Linker 1

<400> SEQUENCE: 13

Ser Gly Gly Gly Gly Ser Gly Gly Gly Gly Thr Gly Gly Gly Gly Ser
1               5                   10                  15

<210> SEQ ID NO 14
```

```
<211> LENGTH: 15
<212> TYPE: PRT
<213> ORGANISM: Artificial
<220> FEATURE:
<223> OTHER INFORMATION: Linker 2

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 357
<212> TYPE: PRT
<213> ORGANISM: Artificial
<220> FEATURE:
<223> OTHER INFORMATION: A26 Fab Heavy-(G4S,G4T,G4S)-645dsFv(gH5)

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Ser Gly Gly Gly
    210                 215                 220

Gly Ser Gly Gly Gly Gly Thr Gly Gly Gly Gly Ser Glu Val Gln Leu
225                 230                 235                 240

Leu Glu Ser Gly Gly Gly Leu Val Gln Pro Gly Gly Ser Leu Arg Leu
                245                 250                 255

Ser Cys Ala Val Ser Gly Ile Asp Leu Ser Asn Tyr Ala Ile Asn Trp
            260                 265                 270

Val Arg Gln Ala Pro Gly Lys Cys Leu Glu Trp Ile Gly Ile Ile Trp
        275                 280                 285

Ala Ser Gly Thr Thr Phe Tyr Ala Thr Trp Ala Lys Gly Arg Phe Thr
    290                 295                 300

Ile Ser Arg Asp Asn Ser Lys Asn Thr Val Tyr Leu Gln Met Asn Ser
```

```
                305                 310                 315                 320
Leu Arg Ala Glu Asp Thr Ala Val Tyr Tyr Cys Ala Arg Thr Val Pro
                    325                 330                 335
Gly Tyr Ser Thr Ala Pro Tyr Phe Asp Leu Trp Gly Gln Gly Thr Leu
                340                 345                 350
Val Thr Val Ser Ser
            355

<210> SEQ ID NO 16
<211> LENGTH: 341
<212> TYPE: PRT
<213> ORGANISM: Artificial
<220> FEATURE:
<223> OTHER INFORMATION: A26 Fab Light-(3xG4S)-645dsFv(gL4)

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
    50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Asp Ile Gln Met Thr Gln Ser Pro Ser Ser Val
225                 230                 235                 240

Ser Ala Ser Val Gly Asp Arg Val Thr Ile Thr Cys Gln Ser Ser Pro
                245                 250                 255

Ser Val Trp Ser Asn Phe Leu Ser Trp Tyr Gln Gln Lys Pro Gly Lys
            260                 265                 270

Ala Pro Lys Leu Leu Ile Tyr Glu Ala Ser Lys Leu Thr Ser Gly Val
        275                 280                 285

Pro Ser Arg Phe Ser Gly Ser Gly Ser Gly Thr Asp Phe Thr Leu Thr
    290                 295                 300

Ile Ser Ser Leu Gln Pro Glu Asp Phe Ala Thr Tyr Tyr Cys Gly Gly
```

```
                305                 310                 315                 320
Gly Tyr Ser Ser Ile Ser Asp Thr Thr Phe Gly Cys Gly Thr Lys Val
                    325                 330                 335
Glu Ile Lys Arg Thr
            340

<210> SEQ ID NO 17
<211> LENGTH: 119
<212> TYPE: PRT
<213> ORGANISM: Artificial
<220> FEATURE:
<223> OTHER INFORMATION: 645gH1 heavy chain variable domain

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Ser Thr Val Tyr Leu Gln Met
65                  70                  75                  80

Asn Ser Leu Arg Ala Glu Asp Thr Ala Val Tyr Tyr Cys Ala Arg Thr
                85                  90                  95

Val Pro Gly Tyr Ser Thr Ala Pro Tyr Phe Asp Leu Trp Gly Gln Gly
            100                 105                 110

Thr Leu Val Thr Val Ser Ser
        115

<210> SEQ ID NO 18
<211> LENGTH: 110
<212> TYPE: PRT
<213> ORGANISM: Artificial
<220> FEATURE:
<223> OTHER INFORMATION: 645gL1 light chain variable domain

<400> SEQUENCE: 18

Asp Ile Val Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Lys
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Cys Gly Thr Lys Val Glu Ile Lys
            100                 105                 110

<210> SEQ ID NO 19
<211> LENGTH: 355
<212> TYPE: PRT
<213> ORGANISM: Artificial
<220> FEATURE:
```

<223> OTHER INFORMATION: A26 Fab Heavy-( 3xG4S)-645dsFv(gH1)

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Ser Gly Gly Gly
    210                 215                 220

Gly Ser Gly Gly Gly Gly Ser Gly Gly Gly Gly Ser Glu Val Gln Leu
225                 230                 235                 240

Leu Glu Ser Gly Gly Gly Leu Val Gln Pro Gly Gly Ser Leu Arg Leu
                245                 250                 255

Ser Cys Ala Val Ser Gly Ile Asp Leu Ser Asn Tyr Ala Ile Asn Trp
            260                 265                 270

Val Arg Gln Ala Pro Gly Lys Cys Leu Glu Trp Ile Gly Ile Ile Trp
        275                 280                 285

Ala Ser Gly Thr Thr Phe Tyr Ala Thr Trp Ala Lys Gly Arg Phe Thr
    290                 295                 300

Ile Ser Arg Asp Ser Thr Thr Val Tyr Leu Gln Met Asn Ser Leu Arg
305                 310                 315                 320

Ala Glu Asp Thr Ala Val Tyr Tyr Cys Ala Arg Thr Val Pro Gly Tyr
                325                 330                 335

Ser Thr Ala Pro Tyr Phe Asp Leu Trp Gly Gln Gly Thr Leu Val Thr
            340                 345                 350

Val Ser Ser
        355
```

<210> SEQ ID NO 20
<211> LENGTH: 340
<212> TYPE: PRT
<213> ORGANISM: Artificial
<220> FEATURE:

<223> OTHER INFORMATION: A26 Fab Light-(3xG4S)-645dsFv(gL1)

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ser Gly Gly Gly Ser Gly Gly Gly Gly
    210                 215                 220

Ser Gly Gly Gly Gly Ser Asp Ile Val Met Thr Gln Ser Pro Ser Ser
225                 230                 235                 240

Val Ser Ala Ser Val Gly Asp Arg Val Thr Ile Thr Cys Gln Ser Ser
                245                 250                 255

Pro Ser Val Trp Ser Asn Phe Leu Ser Trp Tyr Gln Gln Lys Pro Gly
            260                 265                 270

Lys Ala Pro Lys Leu Leu Ile Tyr Glu Ala Ser Lys Leu Thr Ser Gly
        275                 280                 285

Val Pro Ser Arg Phe Lys Gly Ser Gly Ser Gly Thr Asp Phe Thr Leu
    290                 295                 300

Thr Ile Ser Ser Leu Gln Pro Glu Asp Phe Ala Thr Tyr Tyr Cys Gly
305                 310                 315                 320

Gly Gly Tyr Ser Ile Ser Asp Thr Thr Phe Gly Cys Gly Thr Lys
                325                 330                 335

Val Glu Ile Lys
            340

<210> SEQ ID NO 21
<211> LENGTH: 1137
<212> TYPE: DNA
<213> ORGANISM: Artificial
<220> FEATURE:
<223> OTHER INFORMATION: Heavy chain A26-645(gH5) including E.coli OmpA leader

<400> SEQUENCE: 21

```
atgaagaaga ctgctatagc gatcgcagtg gcgctagctg gtttcgccac cgtggcgcaa    60
gctgaagttc agctggtcga gtctggaggc gggcttgtcc agcctggagg gagcctgcgt   120
ctctcttgtg cagcaagcgg tttcacgttc accaactacg gtatccactg gattcgtcag   180
gcaccaggta aggtctggaa tgggtagcc tctatctctc cgtctggtgg tctgacgtac    240
taccgtgact ctgtcaaagg tcgtttcacc atctctcgtg atgacgcgaa aaactctccg   300
tacctgcaaa tgaactctct gcgtgcagaa gataccgcag tgtactactg cgctactggt   360
ggtgaaggta tcttcgacta ctgggtcag ggtaccctgg taactgtctc gagcgcttct    420
acaaagggcc aagcgttttt ccactggct ccgtcctcta atccacctc tggtggtacg     480
gctgcactgg gttgcctggt gaaagactac ttcccagaac cagttaccgt gtcttggaac   540
tctggtgcac tgacctctgg tgttcacacc tttccagcag ttctccagtc ttctggtctg   600
tactccctgt ctagcgtggt taccgttccg tcttcttctc tgggtactca gacctacatc   660
tgcaacgtca accacaaacc gtccaacacc aaggtcgaca aaaaagtcga ccgaaatcc    720
tgtagtggag gtggggctc aggtggaggc gggaccggtg aggtggcag cgaggttcaa     780
ctgcttgagt ctggaggagg cctagtccag cctggaggga gcctgcgtct ctcttgtgca   840
gtaagcggca tcgacctgag caattacgcc atcaactggg tgagacaagc tccggggaag   900
tgtttagaat ggatcggtat aatatgggcc agtgggacga ccttttatgc tacatgggcg   960
aaaggaaggt ttacaattag ccgggacaat agcaaaaaca ccgtgtatct ccaaatgaac  1020
tccttgcgag cagaggacac ggcggtgtac tattgtgctc gcactgtccc aggttatagc  1080
actgcaccct acttcgatct gtggggacaa gggaccctgg tgactgtttc aagttaa     1137
```

<210> SEQ ID NO 22
<211> LENGTH: 1074
<212> TYPE: DNA
<213> ORGANISM: Artificial
<220> FEATURE:
<223> OTHER INFORMATION: Heavy chain A26-645(gH5)

<400> SEQUENCE: 22

```
gaagttcagc tggtcgagtc tggaggcggg cttgtccagc ctggagggag cctgcgtctc    60
tcttgtgcag caagcggttt cacgttcacc aactacggta tccactggat tcgtcaggca   120
ccaggtaaag gtctggaatg ggtagcctct atctctccgt ctggtggtct gacgtactac   180
cgtgactctg tcaaaggtcg tttcaccatc tctcgtgatg acgcgaaaaa ctctccgtac   240
ctgcaaatga actctctgcg tgcagaagat accgcagtgt actactgcgc tactggtggt   300
gaaggtatct tcgactactg gggtcagggt accctggtaa ctgtctcgag cgcttctaca   360
aagggcccaa gcgttttccc actggctccg tcctctaaat ccacctctgg tggtacggct   420
gcactgggtt gcctggtgaa agactacttc ccagaaccag ttaccgtgtc ttggaactct   480
ggtgcactga cctctggtgt tcacaccttt ccagcagttc tccagtcttc tggtctgtac   540
tccctgtcta gcgtggttac cgttccgtct tcttctctgg gtactcagac ctacatctgc   600
aacgtcaacc acaaaccgtc caacaccaag gtcgacaaaa aagtcgagcc gaaatcctgt   660
agtggaggtg ggggctcagg tggaggcggg accggtggag gtggcagcga ggttcaactg   720
cttgagtctg gaggaggcct agtccagcct ggagggagcc tgcgtctctc ttgtgcagta   780
agcggcatcg acctgagcaa ttacgccatc aactgggtga gacaagctcc ggggaagtgt   840
ttagaatgga tcggtataat atgggccagt gggacgacct tttatgctac atgggcgaaa   900
```

| | |
|---|---|
| ggaaggttta caattagccg ggacaatagc aaaaacaccg tgtatctcca aatgaactcc | 960 |
| ttgcgagcag aggacacggc ggtgtactat tgtgctcgca ctgtcccagg ttatagcact | 1020 |
| gcaccctact tcgatctgtg gggacaaggg accctggtga ctgtttcaag ttaa | 1074 |

<210> SEQ ID NO 23
<211> LENGTH: 1089
<212> TYPE: DNA
<213> ORGANISM: Artificial
<220> FEATURE:
<223> OTHER INFORMATION: Light chain A26-645(gL4) including E.coli OmpA leader

<400> SEQUENCE: 23

| | |
|---|---|
| atgaaaaaga cagctatcgc aattgcagtg gcgttggctg gtttcgcgac cgttgcgcaa | 60 |
| gctgatatcc agatgaccca gagcccaagc agtctctccg ccagcgtagg cgatcgtgtg | 120 |
| actattacct gtcgtgcaac ccagagcatc tacaacgctc tggcttggta tcagcagaaa | 180 |
| ccgggtaaag cgccaaaact cctgatctac aacgcgaaca ctctgcatac tggtgttccg | 240 |
| tctcgtttct ctgcgtctgg ttctggtacg gactctactc tgaccatctc ctctctccag | 300 |
| ccggaagatt tcgcgaccta ctactgccag cagtactacg attacccact gacgtttggt | 360 |
| ggtggtacca agttgagat caaacgtacg gttgcagctc catccgtctt catctttcca | 420 |
| ccgtctgacg aacagctcaa atctggtact gcttctgtcg tttgcctcct gaacaacttc | 480 |
| tatccgcgtg aagcgaaagt ccagtggaaa gtcgacaacg cactccagtc tggtaactct | 540 |
| caggaatctg tgaccgaaca ggactccaaa gactccacct actctctgtc tagcaccctg | 600 |
| actctgtcca aagcagacta cgagaaacac aaagtgtacg cttgcgaagt tacccatcag | 660 |
| ggtctgagct ctccggttac caaatccttt aatagagggg agtgtggtgg cggtggcagt | 720 |
| ggtggtggag gttccggagg tggcggttca gacatacaaa tgacccagag tccttcatcg | 780 |
| gtatccgcgt ccgttggcga tagggtgact attacatgtc aaagctctcc tagcgtctgg | 840 |
| agcaattttc tatcctggta tcaacagaaa ccggggaagg ctccaaaact tctgatttat | 900 |
| gaagcctcga aactcaccag tggagttccg tcaagattca gtggctctgg atcagggaca | 960 |
| gacttcacgt tgacaatcag ttcgctgcaa ccagaggact ttgcgaccta ctattgtggt | 1020 |
| ggaggttaca gtagcataag tgatacgaca tttgggtgcg gtactaaggt ggaaatcaaa | 1080 |
| cgtacctaa | 1089 |

<210> SEQ ID NO 24
<211> LENGTH: 1026
<212> TYPE: DNA
<213> ORGANISM: Artificial
<220> FEATURE:
<223> OTHER INFORMATION: Light chain A26-645(gL4)

<400> SEQUENCE: 24

| | |
|---|---|
| gatatccaga tgacccagag cccaagcagt ctctccgcca gcgtaggcga tcgtgtgact | 60 |
| attacctgtc gtgcaaccca gagcatctac aacgctctgg cttggtatca gcagaaaccg | 120 |
| ggtaaagcgc caaaactcct gatctacaac gcgaacactc tgcatactgg tgttccgtct | 180 |
| cgtttctctg cgtctggttc tggtacggac tctactctga ccatctcctc tctccagccg | 240 |
| gaagatttcg cgacctacta ctgccagcag tactacgatt acccactgac gtttggtggt | 300 |
| ggtaccaaag ttgagatcaa acgtacggtt gcagctccat ccgtcttcat ctttccaccg | 360 |
| tctgacgaac agctcaaatc tggtactgct tctgtcgttt gcctcctgaa caacttctat | 420 |

```
ccgcgtgaag cgaaagtcca gtggaaagtc gacaacgcac tccagtctgg taactctcag      480
gaatctgtga ccgaacagga ctccaaagac tccacctact ctctgtctag caccctgact      540
ctgtccaaag cagactacga gaaacacaaa gtgtacgctt gcgaagttac ccatcagggt      600
ctgagctctc cggttaccaa atcctttaat agagggagt gtggtggcgg tggcagtggt       660
ggtggaggtt ccggaggtgg cggttcagac atacaaatga cccagagtcc ttcatcggta      720
tccgcgtccg ttggcgatag ggtgactatt acatgtcaaa gctctcctag cgtctggagc      780
aattttctat cctggtatca acagaaaccg ggaaggctc caaaacttct gatttatgaa       840
gcctcgaaac tcaccagtgg agttccgtca agattcagtg gctctggatc agggacagac      900
ttcacgttga caatcagttc gctgcaacca gaggactttg cgacctacta ttgtggtgga      960
ggttacagta gcataagtga tacgacattt gggtgcggta ctaaggtgga atcaaacgt     1020 acctaa                                                               1026
```

<210> SEQ ID NO 25
<211> LENGTH: 1131
<212> TYPE: DNA
<213> ORGANISM: Artificial
<220> FEATURE:
<223> OTHER INFORMATION: Heavy chain A26-645(gH5) including B72.3 leader
      sequence

<400> SEQUENCE: 25

```
atggaatggt cctgggtctt cctgtttttc ctttctgtca caaccggggt gcacagcgag       60
gtgcagctcg tcgagtctgg aggcgggctt gtccagcctg gagggagcct gcgtctctct      120
tgtgcagcaa gcggtttcac gttcaccaac tacggtatcc actggattcg tcaggcacca      180
ggtaaaggtc tggaatgggt agcctctatc tctccgtctg gtggtctgac gtactaccgt      240
gactctgtca aaggtcgttt caccatctct cgtgatgacg cgaaaaactc tccgtacctg      300
cagatgaact ctctgcgtgc agaagatacc gcagtgtact actgcgctac tggtggtgaa      360
ggtatcttcg actactgggg tcagggtacc ctggtaactg tctcaagcgc ttctacaaag      420
ggcccatcgg tcttccccct ggcacccctcc tccaagagca cctctggggg cacagcggcc      480
ctgggctgcc tggtcaagga ctacttcccc gaaccggtga cggtgtcgtg aactcaggc       540 gccctgacca gcggcgtgca caccttcccg gctgtcctac agtcctctgg actctactcc      600
ctcagcagcg tggtgaccgt gccctccagc agcttgggca cccagaccta catctgcaac      660
gtgaatcaca agcccagcaa caccaaggtg gacaagaaag ttgagcccaa atcttgttcc      720
ggaggtggcg gttccggagg tggcggtacc ggtggcggtg gatccgaagt ccagctgctt      780
gaatccggag gcggactcgt gcagcccgga ggcagtcttc gcttgtcctg cgctgtatct      840
ggaatcgacc tgagcaatta cgccatcaac tgggtgagac aggcacctgg gaaatgcctc      900
gaatggatcg gcattatatg ggctagtggg acgaccttt atgctacatg gcgaagggt       960 agattcacaa tctcacggga taatagtaag aacacagtgt acctgcagat gaactccctg     1020
cgagcagagg ataccgccgt ttactattgt gctcgcactg tcccaggtta tagcactgca     1080
ccctactttg atctgtgggg gcagggcact ctggtcaccg tctcgagttg a              1131
```

<210> SEQ ID NO 26
<211> LENGTH: 1074
<212> TYPE: DNA
<213> ORGANISM: Artificial
<220> FEATURE:
<223> OTHER INFORMATION: Heavy chain A26-645(gH5)

<400> SEQUENCE: 26

| | | | | | |
|---|---|---|---|---|---|
| gaggtgcagc | tcgtcgagtc | tggaggcggg | cttgtccagc | ctggagggag | cctgcgtctc | 60 |
| tcttgtgcag | caagcggttt | cacgttcacc | aactacggta | tccactggat | tcgtcaggca | 120 |
| ccaggtaaag | gtctggaatg | gtagcctct | atctctccgt | ctggtggtct | gacgtactac | 180 |
| cgtgactctg | tcaaaggtcg | tttcaccatc | tctcgtgatg | acgcgaaaaa | ctctccgtac | 240 |
| ctgcagatga | actctctgcg | tgcagaagat | accgcagtgt | actactgcgc | tactggtggt | 300 |
| gaaggtatct | tcgactactg | gggtcagggt | accctggtaa | ctgtctcaag | cgcttctaca | 360 |
| aagggcccat | cggtcttccc | cctggcaccc | tcctccaaga | gcacctctgg | ggcacagcg | 420 |
| gccctgggct | gcctggtcaa | ggactacttc | cccgaaccgg | tgacggtgtc | gtggaactca | 480 |
| ggcgccctga | ccagcggcgt | gcacaccttc | ccggctgtcc | tacagtcctc | tggactctac | 540 |
| tccctcagca | gcgtggtgac | cgtgccctcc | agcagcttgg | gcacccagac | ctacatctgc | 600 |
| aacgtgaatc | acaagcccag | caacaccaag | gtggacaaga | aagttgagcc | caaatcttgt | 660 |
| tccggaggtg | gcggttccgg | aggtggcggt | accggtggcg | gtggatccga | agtccagctg | 720 |
| cttgaatccg | gaggcggact | cgtgcagccc | ggaggcagtc | ttcgcttgtc | ctgcgctgta | 780 |
| tctggaatcg | acctgagcaa | ttacgccatc | aactgggtga | cacaggcacc | tgggaaatgc | 840 |
| ctcgaatgga | tcggcattat | atgggctagt | gggacgacct | tttatgctac | atgggcgaag | 900 |
| ggtagattca | caatctcacg | ggataatagt | aagaacacag | tgtacctgca | gatgaactcc | 960 |
| ctgcgagcag | aggataccgc | cgtttactat | tgtgctcgca | ctgtcccagg | ttatagcact | 1020 |
| gcaccctact | ttgatctgtg | ggggcagggc | actctggtca | ccgtctcgag | ttga | 1074 |

<210> SEQ ID NO 27
<211> LENGTH: 1086
<212> TYPE: DNA
<213> ORGANISM: Artificial
<220> FEATURE:
<223> OTHER INFORMATION: Light chain A26-645(gL4) including B72.3 leader sequence

<400> SEQUENCE: 27

| | | | | | |
|---|---|---|---|---|---|
| atgtcagttc | ccacacaggt | gctgggcctg | cttctgttgt | ggctcaccga | tgctaggtgt | 60 |
| gatatccaga | tgacccagag | tccaagcagt | ctctccgcca | gcgtaggcga | tcgtgtgact | 120 |
| attacctgtc | gtgcaaccca | gagcatctac | aacgctctgg | cttggtatca | gcagaaaccg | 180 |
| ggtaaagcgc | caaaactcct | gatctacaac | gcgaacactc | tgcataccgg | tgttccgtct | 240 |
| cgtttctctg | cgtctggttc | tggtacggac | tctactctga | ccatctcctc | tctgcagccg | 300 |
| gaagatttcg | cgacctacta | ctgccagcag | tactacgatt | acccactgac | gtttggtggt | 360 |
| ggtaccaaag | ttgagatcaa | acgtacggtg | gctgcaccat | ctgtcttcat | cttcccccca | 420 |
| tctgatgagc | agttgaagtc | tggcactgcc | tctgttgtgt | gcctgctgaa | taacttctac | 480 |
| cctagagagg | ccaaagtcca | gtggaaggtg | gataacgccc | tcaatccgg | aaactcccag | 540 |
| gagagtgtca | ctgagcagga | ctcaaaggac | tccacctata | gccttagcag | cacactgaca | 600 |
| ctgagcaagg | ctgactacga | gaaacacaag | gtctacgcct | cgaagtgac | acatcaaggc | 660 |
| ctgagctcac | ccgtgacaaa | gagctttaac | aggggagagt | gtggtggagg | tggctctggc | 720 |
| ggtggtggct | ccggaggcgg | aggaagcgac | atccagatga | cccagagccc | ttcctctgta | 780 |
| agcgccagtg | tcggagacag | agtgactatt | acctgccaaa | gctccccttc | agtctggtcc | 840 |
| aatttttctat | cctggtacca | gcaaaagccc | ggaaaggctc | ctaaattgct | gatctacgaa | 900 |

```
gcaagcaaac tcaccagcgg cgtgcccagc aggttcagcg gcagtgggtc tggaactgac    960
tttaccctga caatctcctc actccagccc gaggacttcg ccacctatta ctgcggtgga   1020
ggttacagta gcataagtga tacgacattt ggatgcggca ctaaagtgga aatcaagcgt   1080
acctga                                                              1086

<210> SEQ ID NO 28
<211> LENGTH: 1026
<212> TYPE: DNA
<213> ORGANISM: Artificial
<220> FEATURE:
<223> OTHER INFORMATION: Light chain A26-645(gL4)

<400> SEQUENCE: 28
gatatccaga tgacccagag tccaagcagt ctctccgcca gcgtaggcga tcgtgtgact     60
attacctgtc gtgcaaccca gagcatctac aacgctctgg cttggtatca gcagaaaccg    120
ggtaaagcgc caaaactcct gatctacaac gcgaacactc tgcataccgg tgttccgtct    180
cgtttctctg cgtctggttc tggtacggac tctactctga ccatctcctc tctgcagccg    240
gaagatttcg cgacctacta ctgccagcag tactacgatt acccactgac gtttggtggt    300
ggtaccaaag ttgagatcaa acgtacggtg gctgcaccat ctgtcttcat cttcccccca    360
tctgatgagc agttgaagtc tggcactgcc tctgttgtgt gcctgctgaa taacttctac    420
cctagagagg ccaaagtcca gtggaaggtg gataacgccc ttcaatccgg aaactcccag    480
gagagtgtca ctgagcagga ctcaaaggac tccacctata gccttagcag cacactgaca    540
ctgagcaagg ctgactacga aaacacaag gtctacgcct gcgaagtgac acatcaaggc    600
ctgagctcac ccgtgacaaa gagctttaac aggggagagt gtggtggagg tggctctggc    660
ggtggtggct ccggaggcgg aggaagcgac atccagatga cccagagccc ttcctctgta    720
agcgccagtg tcggagacag agtgactatt acctgccaaa gctccccttc agtctggtcc    780
aattttctat cctggtacca gcaaaagccc ggaaaggctc ctaaattgct gatctacgaa    840
gcaagcaaac tcaccagcgg cgtgcccagc aggttcagcg gcagtgggtc tggaactgac    900
tttaccctga caatctcctc actccagccc gaggacttcg ccacctatta ctgcggtgga    960
ggttacagta gcataagtga tacgacattt ggatgcggca ctaaagtgga aatcaagcgt   1020
acctga                                                              1026
```